US006913753B2

(12) United States Patent
Ramachandran et al.

(10) Patent No.: US 6,913,753 B2
(45) Date of Patent: *Jul. 5, 2005

(54) INCAPACITATED WHOLE-CELL IMMUNOGENIC BACTERIAL COMPOSITIONS

(75) Inventors: Janakiraman Ramachandran, Palo Alto, CA (US); Sriram Padmanabhan, Sanjaynagar (IN); Bharathi Sriram, Sanjaynagar (IN)

(73) Assignee: Gangagen, Inc., Palo Alto, CA (US)

( * ) Notice: Subject to any disclaimer, the term of this patent is extended or adjusted under 35 U.S.C. 154(b) by 77 days.

This patent is subject to a terminal disclaimer.

(21) Appl. No.: 10/259,164

(22) Filed: Sep. 27, 2002

(65) Prior Publication Data

US 2003/0152589 A1 Aug. 14, 2003

Related U.S. Application Data

(60) Provisional application No. 60/325,796, filed on Sep. 27, 2001.

(51) Int. Cl.$^7$ ............................................. A61K 39/02
(52) U.S. Cl. ................. 424/234.1; 424/243.1; 424/257.1; 424/256.1; 424/249.1; 424/259.1; 424/93.1; 424/93.2; 424/93.4; 424/93.6; 435/252.3; 435/320.1
(58) Field of Search .......................... 424/234.1, 243.1, 424/257.1, 256.1, 249.1, 259.1, 93.1, 93.2, 93.4, 93.6; 435/252.3, 320.1

(56) References Cited

U.S. PATENT DOCUMENTS 4,376,110 A 3/1983 David et al.
6,130,082 A 10/2000 Majararian et al.

OTHER PUBLICATIONS

Longchamp et al. 1996. Abstracts of the Gen.Meet. of Amer.Soc. for Microbiol., May 19–23, p. 576.*
Devine et al. J.Bacteriol. 1977. 129(2): 1072–1077.*
Grundling et al. J.Bacteriol. Nov. 2000. 182(21): 6082–6090.*
The American Heritage Dictionary of the English Language. 4$^{th}$ edition. 2000. entry "incapacitated".*
Ackermann, "Tailed bacteriophages: the order caudovirales," Adv Virus Res, 51:135–201. (1998).
Arendt et al., Molecular Characterization of Lactorcoccal Bacteriophage Tuc2009 and Identification and Analysis of Genes Encoding Lysin, a Putative Holin, and Two Structural Proteins, Applied and Environment Microbiology, Jun. 1994, p. 1875–1883, vol. 60, No. 6.
Auad et al., "Physical mapping and partial genetic characterization of the Lactobacillus delbrueckii subsp. bulgaricus bacteriophage lb539," Arch Virol, 144: 1503–1512. (1999).

Boizet et al., "Cloning, expression and sequence analysis of an endolysin–encoding gene of Lactobacillus bulgaricus bacteriophage mv1." Gene, 94: 61–67 (1990).
Botstein et al., "Strategies and Applications of in Vitro Mutagenesis," Science 229, vol. 229, p. 1193–1201, No. 4719 (1985).
Calandra et al., "Cellular streptolysin S–related hemolysins of group A Streptococcus C203S," Infect Immun, 12: 13–28. (1975).
Calandra et al., "Lysis and protoplast formation of group B streptococci by mutanolysin," Infect Immun, 28: 1033–1037 (1980).
Caldentey et al., The Lytic Enzyme of the Pseudommonas Phage Φ6. Purification and Biochemical Characterization, Biochimica et Biophysica Acta, 1159, 44–50 (1992).
Cattozzo et al., "Expression and Immunogenicity of $V_3$ Loop Epitopes of HIV–1, Isolates SC and WMJ2, Inserted in Salmonella Flagellin," Journal Biotechnology 56 (1997) 191–203.
Chalfie et al., "Green Fluorescent Protein as a Marker for Gene Expression," Science, vol. 263, 802–805 1994.
Chandry et al., "Analysis of the DNA sequence, gene expression, origin of replication and modular structure of the Lactococcus lactis lytic bacteriophage sk1," Mol. Microbiol, 26: 49–64 (1997).
Cohen et al., "Simple procedure for production by group C streptococci of phage– associated lysin active against group A streptococci," Appl Microbiol, 29: 175–178 (1975).
Cole et al., "The EBV–hybridoma technique and its application to human lung cancer," Monoclonal Antibodies And Cancer Therapy, Alan R. Liss, Inc., pp. 77–96 (1985).
Cote et al., "Generation of human monoclonal antibodies reactive with cellular antigens," Proc. Natl. Acad. Sci. USA 80: 2026–2030 (1983).
Coleman et al., "Cloning and expression in Escherichia coli and Straphylococcus aureus of the beta–lysin determinant from Staphylococcus aureus: evidence that bacteriophage conversion of beta–lysin activity is caused by insertional inactivation of the beta–lysin determinant," Microb Pathog, 1: 549–564 (1986).

(Continued)

Primary Examiner—Jennifer E. Graser
(74) Attorney, Agent, or Firm—Carol L. Francis; Bozicevic, Field & Francis LLP

(57) ABSTRACT

The invention features incapacitated whole cell bacterial immunogenic compositions produced by infecting a bacterium with Lys minus bacteriophage, which are deficient in the lysin protein. Lys minus bacteriophage retain activity in infection of its appropriate bacterial host, destruction of the bacterial genome, and replication, which are sufficient to inhibit bacterial growth and replication. The resulting, Lys minus-infected bacterium is provided in a state of bacteriostasis, and is not capable of replicating further (e.g., is "incapacitated"). The incapacitated bacterium can then be used as to elicit an immune response for prophylactic and/or therapeutic purposes. The invention thus also features incapacitated bacteria formulated appropriately for use in immunogenic compositions for eliciting an immune response, e.g., for production of antibodies in a non-human host or in a whole cell bacterial vaccine.

17 Claims, 5 Drawing Sheets

OTHER PUBLICATIONS

Coleman et al., *Staphylococcus aureus* bacteriophages mediating the simultaneous lysogenic conversion of beta–lysin, staphylokinase and enterotoxin A: molecular mechanism of triple conversion. *J Gen Microbiol*, 135.

Cooney et al., "Molecular cloning and genetic analysis of the determinant for gamma– lysin, a two–component toxin of Staphylococcus aureus," *J Gen Microbiol*, 134:2179–2188 (1988).

Cormack, et al., "FACS–optimized mutants of the green fluorescent protein (GFP)," *Gene*, 173, 33–38 (1996).

de Ruyter et al., "Food–grade controlled lysis of *Lactococcus lactis* for accelerated cheese ripening," *Nat Biotechnol*, 15: 976–979 (1997).

Diaz et al., "The two–step lysis system of pneumococcal bacteriophage EI–1 is functional in gram–negative bacteria: triggering of the major pneumococcal autolysin in *Escherichia coli*," *Mol Microbiol*, 19: 667–681.

Dietrich et al., "Delivery of antigen–encoding plasmid DNA into the cytosol of macrophages by attenuated suicide *Listeria monocytogenes*," *Nat Biotechnol*, 16: 181–185 (1998).

Elias et al., "*Staphylococcus aureus* haemolysins: their use in strain typing," *Acta Microbiol Acad Sci Hung*, 27: 183–190 (1980).

Fischetti et al., "Purification and physical properties of group C streptococcal phage– associated lysine," *J Exp Med*, 133: 1105–1117 (1971).

Gaeng et al., "Gene cloning and expression and secretion of listeria monocytogenes bacteriophage–lytic enzymes in lactococcus lactis," Appl. Environ. Microbiol. 66, 2951 (2000).

Garcia et al., "Biochemical characterization of a murein hydrolase induced by bacteriophage Dp–1 in *Streptococcus pneumoniae*: comparative study between bacteriophage–associated lysin and the host amidase," *J*.

Garcia et al., "Cloning, purification, and biochemical characterization of the pneumococcal bacteriophage Cp–1 lysin," *J Virol*, 61: 2573–2580 (1987).

Garcia et al., "Mechanism of phage–induced lysis in pneumococci." J Gen Microbiol, 129: 479–487. (1983).

Garrett, "Cell Lysis by induction of cloned lambda lysis genes," J. et al. Mol. Gen. Genet. 182, 326 (1981).

Garvey et al., "Nucleotide sequence of bacillus phage Φ29 genes 14 and 15: homology of gene 15 with other phage lysozymes," Nucleic Acids Res. 14, 10001 (1986).

Gindreau et al., "Molecular analysis of the region encoding the lytic system from *Oenococcus oeni* temperate bacteriophage phi 10MC," *FEMS Microbiol Lett*, 171: 231–238 (1999).

Henikoff, "Undirectional digestion with exonuclease III creates targeted breakpoints for DNA sequencing," Gene 28, 351 (1984).

Henrich et al., "Primary structure and functional analysis of the lysis genes of *Lactobacillus gasseri* bacteriophage phi adh," *J Bacteriol*, 177: 723–732 (1995).

Higuchi et al., "A general method of in vitri preparation and specific mutagenesis of DNA fragments: study of protein and DNA interactions," Nucleic Acids Res. 16, 7351 (1988).

Hill et al., Identification of a lysin associated with a bacteriophage (A25) virulent for group A streptococci. *J Bacteriol*, 145: 696–703 (1981).

Inouye et al., "Bacteriophage T7 lysozyme is an n–acetyl-muramyl–Lalanine amidase" Biol.Chem. 248, 7247 (1973).

Jain et al., "Use of lambda phage s and r gene products in an inducible lysis system for vibrio cholerae– and salmonella enterica serovar typhimurium–based DNA vaccine delivery systems," Infect Immun, 68, 986 (2000).

Jerne, "Towards a network theory of the immune system," Ann. Immunol. (Paris) 125c:373–389 (1974).

Jerne, N. K., et al., "Recurrent idiotopes and internal images," EMBO 1:234 (1982).

Kaneko et al., "Complete nucleotide sequence and molecular characterization of the temperate staphylococcal bacteriophage phiPVL carrying Panton–Valentine leukocidin genes," *Gene*, 215:57–67 (1998).

Kohler et al., "Continuous cultures of fused cells secreting antibody of predefined specificity," Nature 256, 495–497 (1975).

Kosbor et al., "The production of monoclonal antibodies from human lymphocytes," Immunology Today 4, 72 (1983).

Loessner et al., "Heterogeneous endolysins in Listeria monocytogenes bacteriophages: a new class of enzymes and evidence for conserved holin genes within the siphoviral lysis cassettes," *Mol Microbiol*, 16: 1231–1241.

Loessner et al., "Modified Listeria bacteriophage lysin genes (ply) allow efficient overexpression and one–step purification of biochemically active fusion proteins," *Appl Environ Microbiol*, 62: 3057–3060 (1996).

Martin et al. (1998) "Functional analysis of the two–gene lysis system of the pneumococcal phage Cp–1 in homologous and heterologous host cells," *J Bacteriol*, 180:210–217 (1998).

Mermod et al., "Vector for regulated expression of cloned genes in a wide range of gram–negative bacteria," J. Bacteriol. 167, 447(1986).

Mindich et al., "Cell wall lysin as a component of the bacteriophage phi 6 virion," *J Virol*, 30: 489–496 (1979).

Mullan et al., "Lysin production by phi C2(W), a prolate phage for *Streptococcus lactis* C2," *J Dairy Res*, 52: 113–121 (1985).

Mullan et al., "Partial purification and some properties of phi (C2(W) lysin, a lytic enzyme produced by phage–infected cells of *Streptococcus lactis* C2," *J Dairy Res*, 52:123–138 (1985).

Nelson et al., "Prevention and elimination of upper respiratory colonization of mice by group A streptococci by using a bacteriophage lytic enzyme," *Proc Natl Acad Sci U S A*, 98: 4107–4112 (2001).

Newton et al., "Expression and immunogenicity of an 18–residue epitope of HIV1 gp41 inserted in the flagellar protein of a salmonella live vaccine," Res. Microbiol. 146, 203–216 (1995).

Newton et al., "Immune response to cholera toxin epitope inserted in salmonella flagellin," Science 244, 70 (1989).

Norrby, E., Summary, in Vaccines 85, Lerner, R. A., R. M. Chanock, and F. Brown (eds.), Cold Spring Harbor Laboratory, Cold Spring Harbor, N.Y., pp. 388–389 (1985).

Oki et al., "Cloning, sequence analysis, and expression of the genes encoding lytic functions of Bacteriophage phi g1e," *Gene*, 176: 215–223 (1996).

Owen et al, "Nucleotide sequence of the lysozyme gene of bacteriophage T4—analysis of mutations involving repeated sequences," *J. Mol. Biol. 165*, 229 (1983) Schmidt et al. J. Bacteriol. 178, 1099 (1983).

Payne et al., "Exploitation of a chromosomally integrated lactose operon for controlled gene expression in Lactococcus lactis," FEMS Microbiol Lett, 136: 19–24 (1996).

Raina, "Purification of Streptococcus group C bacteriophage lysine," *J Bacteriol*, 145: 661–663 (1981).

Rennell et al., "Phage P22 lysis genes: nucleotide sequences and functional relationships with T4 and λ genes," Virol. 143, 280 (1985).

Rosenberg, et al., "Regulatory sequences involved in the promotion and termination of RNA transcription," Ann. Rev. Genet. 13, 319–53 (1979).

Sable et al., "The lysins of bacteriophages infecting lactic acid bacteria," *Appl Microbiol Biotechnol*, 43: 1–6 (1995).

Sanders et al., "A chloride–inducible gene expression cassette and its use in induced lysis of *Lactococcus lactis. Appl Environ Microbiol*," vol. 63, No. 12, 4877–4882 (1997).

Schmidt et al., "Three functions of bacteriophage p1 involved in cell lysis," J. Bacteriol., vol. 178, No. 4, 1099–1104 (1996).

Shearman et al., "Cloning and DNA sequence analysis of a Lactococcus bacteriophage lysin gene," *Mol Gen Genet*, 218: 214–221 (1989).

Shearman et al., "Controlled expression and structural organization of a *Lactococcus lactis* bacteriophage lysin encoded by two overlapping genes," *Appl Environ Microbiol*, 60: 3063–3073 (1994).

Sheehan et al., "Analysis of the catalytic domain of the lysin of the lactococcal bacteriophage Tuc2009 by chimeric gene assembling." *FEMS Microbiol Lett*, 140: 23–28 (1996).

Sheehan et al., "The lytic enzyme of the penumococcal phage Dp–1: a chimeric lysin of intergeneric origin." *Mol Microbiol*, 25: 717–725 (1997).

Sheehan et al., "Identification and characterization of a lysis module present in a large proportion of bacteriophages infecting *Streptococcus thermophilus*." Appl Environ Microbiol, 65: 569–577 (1999).

Shortle et al., "Gap misrepair mutagenesis: efficient site–directed induction of transition, transversion, and frameshift mutations in vitro." Proc.Natl.Acad.Sci.USA 79, 1588 (1982).

Singer, "Determination of the amount of homology required for recombination in bacteriophage T4." Cell, 31: 25–33 (1982).

Smith, "In vitro mutagenesis," Ann. Rev. Genet. 19, 423–462 (1985).

Sonstein et al., "Staphylococcal bacteriophage–associated lysin: a lytic agent active against *Staphylococcus aureus*," *J Bacteriol*, 107: 499–504. (1971).

Spicer and Konigsberg in Bacteriophage T4 eds. Mathews, Kutter, Mosig and Berget, American Society for Microbiology, Washington, DC, 1983 , pp. 299.

Stocker et al, "Immune responses to epitopes inserted in salmonella flagellin," Int. Rev. Immunol. 11, 167 (1994).

Stocker, "Aromatic–dependent salmonella as live vaccine presenters of foreign epitopes as inserts in flagellin," Res. Microbiol. 141, 787–796 (1990).

Streisinger et al., "Mutations affecting the lysozyme of phage T4," Cold Spring Harbor Symp. Quant. Biol. 26, 25–30 (1961).

Tourville et al., "Lactic streptococcal phage–associated lysin. I. Lysis of heterologous lactic streptococci by a phage–induced lysin." *J Dairy Sci*, 49: 158–162 (1966).

Tsugita et al., "Purification of bacteriophage T4 lysozyme" J. Biol. Chem. 243, 391 (1968).

Vallette et al., "Construction of mutant and chimeric genes using the polymerase chain reaction," Nucleic Acids Res. 17, 723 (1989).

van der Vijver et al., "Induction of mutation in *Staphylococcus aureus* by ethylmethane sulphonate." *J Med Microbiol*, 8: 265–277 (1975).

van Sinderen et al., "Sequence analysis and molecular characterization of the temperature lactococcal bacteriophage rlt." *Mol Microbiol*, 19: 1343–1355 (1996).

Volker et al., Induction of mutations in specific genes of bacteriophage T4 using cloned restriction fragments and marker rescue Mol. Gen. Genet. 177, 447 (1980).

Wang et al., "Holins: The protein clocks of bacteriophage infections," Ann. Rev. Microbiol. 54, 799–825 (2000).

Ward et al., "Sequence analysis of the lysin gene region of the prolate lactococcal bacteriophage c2," *Can J Microbiol*, 39: 767–774 (1993).

Wheeler et al., "Production of group C streptococcus phage–associated lysin and the preparation of *Streptococcus pyogenes* protoplast membranes." *J Gen Microbiol*, 120:27–33 (1980).

Wilson, I. A., et al., "The structure of an antigenic determinant in a protein," Cell 37:767 (1984).

Yoon et al., "Characterization of a lytic *Lactobacillus plantarum* bacteriophage and molecular cloning of a lysin gene in *Escherichia coli*.," Int J Food Microbiol, 65: 63–64. (2001).

Young, "Bacteriophage lysis: mechanism and regulation." Microbiol Rev, 56:430–481 (1992).

Zhao et al., "Polymerase chain reaction–based point mutagenesis protocol," Methods Enzymol. 217, 218 (1993).

Ziermann et al., "Functions involved in bacteriophage P2–induced host cell lysis and identification of a new tail gene," J. Bacteriol. vol. 176, No. 16, 4974 (1994).

Bernhardt, et al., "*Genetic Evidence that the Bacteriophage OX174 Lysis Protein Inhibits Cell Wall Synthesis*" Proc. Natl. Acad Sci. vol. 97, No. 8, pp. 4297–4302 (Apr. 2000).

\* cited by examiner

INCAPACITATED WHOLE-CELL IMMUNOGENIC BACTERIAL COMPOSITIONS

CROSS-REFERENCE TO RELATED APPLICATIONS

This application claims the benefit of prior U.S. Provisional Application Ser. No. 60/325,796, filed Sep. 27, 2001, which application is incorporated herein by reference.

FIELD OF THE INVENTION

The invention relates to methods and compositions for production of whole-cell, inactivated immunogenic bacterial compositions that are very similar to the live infectious pathogen but are not infectious.

BACKGROUND OF THE INVENTION

The alarming increase in bacterial resistance to available antibiotics, international travel and newly identified infectious diseases have highlighted the need for new effective vaccines. Inactivated whole-cell vaccines are an important component of the approaches emerging to meet these public health needs. The administration of whole-cell vaccines is one of the most well-studied methods of vaccination against bacterial infection. The particular advantages of whole-cell vaccines include the presentation of many antigens (including protective, but yet undefined antigens), minimal chances of side effects when given non-parenterally, zero virulence potential, and adjuvant-like character. Studies in animal models and humans have shown immunogenicity when whole-cell vaccines were administered orally or parenterally. Effective protection against respiratory, enteric, and systemic bacterial infections has also been shown. Although only inactivated whole-cell pertussis vaccine has been used to immunize the general public, other whole-cell vaccines have the potential for global use.

There are only two basic types of whole-cell vaccines: live attenuated and inactivated. The characteristics of live and inactivated vaccines are different, and these characteristics determine how the vaccine is used.

Live Attenuated Vaccines

Live attenuated vaccines are produced by modifying a disease-producing ("wild") bacteria in the laboratory. Live attenuated vaccines available in the U.S. include live viruses and live bacteria. These wild viruses or bacteria are attenuated, or weakened, in the laboratory, usually by repeated culturing. In order to produce an immune response, live attenuated vaccines must replicate (grow) in the vaccinated person. A relatively small dose of virus or bacteria is given, which replicates in the body and increases to a volume large enough to stimulate an immune response. Anything that either damages the live organism in the vial (e.g., heat, light), or interferes with replication of the organism in the body (circulating antibody) can cause the vaccine to be ineffective. Although live attenuated vaccines replicate, they usually do not cause disease, such as may occur with the natural ("wild") organism. When a live attenuated vaccine does cause "disease," it is usually much milder than the natural disease, and is referred to as an adverse reaction. The immune response to a live attenuated vaccine is virtually identical to that produced by a natural infection. The immune system does not differentiate between an infection with a weakened vaccine bacterium and an infection with a wild-type bacterium. Live attenuated vaccines are generally effective with one dose, except those administered orally.

However, live attenuated vaccines meet with several limitations. First, live attenuated vaccines may cause severe or fatal reactions as a result of uncontrolled replication (growth) of the vaccine virus. This only occurs in persons with immunodeficiency (e.g., from leukemia, treatment with certain drugs, or HIV infection). In addition, depending upon how the vaccine strain was generated, a live attenuated vaccine can sometimes revert back to its original pathogenic (disease-causing) form. To date, this has only been known to occur with live polio vaccine. Active immunity from a live attenuated vaccine may not develop due to interference from circulating antibody to the vaccine virus. Antibody from any source (e.g., transplacental, transfusion) can interfere with growth of the vaccine organism and lead to nonresponse to the vaccine (also known as vaccine failure). Measles vaccine virus seems to be most sensitive to circulating antibody. Polio and rotavirus vaccine viruses are least affected. Live attenuated vaccines are labile, and can be damaged or destroyed by heat and light. They must be handled and stored carefully. Currently available live attenuated vaccines include live viruses (measles, mumps, rubella, polio, yellow fever, vaccinia, and varicella), and two live bacterial vaccines (BCG and oral typhoid).

Inactivated Vaccines

Inactivated vaccines can be composed of either whole viruses or bacteria, or fractions of either. Fractional vaccines are either protein-based or polysaccharide-based. Protein-based vaccines include toxoids (inactivated bacterial toxin), and subunit products. Most polysaccharide-based vaccines are composed of pure cell-wall polysaccharide from bacteria. Conjugate polysaccharide vaccines are those in which the polysaccharide is chemically linked to a protein. This linkage makes the polysaccharide a more potent vaccine. These vaccines are produced by growing the bacteria in culture media, then inactivating it with heat and/or chemicals (usually formalin). In the case of fractional vaccines, the organism is further treated to purify only those components to be included in the vaccine (e.g., the polysaccharide capsule of pneumococcus).

Inactivated vaccines are not alive and cannot replicate. The entire dose of antigen is administered in the injection (as compared to live attenuated vaccines, which provide further "doses" upon replication in the host). Inactivated vaccines cannot cause disease from infection, even in an immunodeficient person. Unlike live antigens, inactivated antigens are usually not affected by circulating antibody. Inactivated vaccines may be given when antibody is present in the blood (e.g., in infancy, or following receipt of antibody-containing blood products). Inactivated vaccines always require multiple doses. In general, the first dose does not produce protective immunity, but only "primes" the immune system. A protective immune response develops after the second or third dose.

In contrast to live vaccines, in which the immune response closely resembles natural infection, the immune response to an inactivated vaccine is mostly humoral. Little or no cellular immunity results. Antibody titers against inactivated antigens fall over time. As a result, some inactivated vaccines may require periodic supplemental doses to increase, or "boost," antibody titers. In some cases, the antigen critical to protection against the disease may not be defined, thus requiring the use of "whole cell" vaccines. Currently available inactivated vaccines include inactivated whole viruses (influenza, polio, rabies, hepatitis A) and inactivated whole bacteria (pertussis, typhoid, cholera, plague). "Fractional" vaccines include subunits (hepatitis B, influenza, acellular pertussis, typhoid Vi, Lyme disease), toxoids (diphtheria, tetanus, botulinum), pure polysaccharides (pneumococcal, meningococcal, *Haemophilus influenzae* type b), and polysaccharide conjugates (*Haemophilus influenzae* type b and pneumococcal).

In summary, it is recognized that the more similar a vaccine is to the natural disease, the better the immune response to the vaccine. While attenuated vaccines are most promising in this regard, they pose risks of disease in immunocompromised hosts and reversion to wild-type, pathogenic organisms. Inactivated vaccines avoid these problems, but yet can be less desirable in that these vaccines do not mimic natural infection and so may not elicit the relevant immune response or elicit as robust, protective an immune response as might be desired.

There is thus a need in the field for safe bacterial vaccines that resemble the infectious organism more closely than the inactivated vaccines, but which have reduced or no significant risk of causing disease in the vaccinated subject. The present invention addresses this need.

SUMMARY OF THE INVENTION

The invention features incapacitated whole cell bacterial immunogenic compositions produced by infecting a bacterium with a Lys minus bacteriophage, which are deficient in the lysin protein. Lys minus bacteriophage are incapable of facilitating efficient lysis of the bacterial host since the enzymatic activity of the lysin of the phage is needed for enzymatic degradation of the peptidoglycan layer of the bacterial cell wall. Lys minus bacteriophage retain activity in infection of its appropriate bacterial host, destruction of the bacterial genome, and replication, which are sufficient to inhibit bacterial growth and replication. The resulting, Lys minus-infected bacterium is provided in a state of bacteriostasis, and is not capable of replicating further (e.g., is "incapacitated"). The incapacitated bacterium can then be used as to elicit an immune response for prophylactic and/or therapeutic purposes. The invention thus also features incapacitated bacteria formulated appropriately for use in immunogenic compositions for eliciting an immune response, e.g., for production of antibodies in a non-human host or in a whole cell bacterial vaccine.

In one aspect the invention features a method of eliciting an immune response to a bacterial pathogen, the method comprising administering an incapacitated whole cell immunogenic bacterial composition to a subject susceptible to infection by or a disease caused by a pathogenic bacterium. The composition comprises the pathogenic bacterium incapacitated by infection with a lysis-defective bacteriophage, and is administered in an amount effective to elicit an immune response to the pathogenic bacterium in the host.

In another aspect, the invention features a method of eliciting in a subject a protective immune response against disease caused by a bacterial pathogen, the method comprising administering to a subject susceptible to disease caused by a pathogenic bacterium an incapacitated whole cell immunogenic bacterial composition. The composition comprises the pathogenic bacterium incapacitated by infection with a lysis-defective bacteriophage, and is administered in an amount effective to elicit a protective immune response to the pathogenic bacterium in the host.

In yet another aspect, the invention features a method for eliciting an immune response to an antigen, the method comprising administering to a subject an incapacitated whole cell bacterial composition. The composition comprises a bacterium incapacitated by infection with a lysis-defective bacteriophage, and is administered in an amount effective to elicit an immune response in the subject to an antigen present in or on the bacterium. In specific embodiments, the antigen is a bacterial antigen endogenous to the bacterium or a recombinant antigen. In some embodiments the recombinant antigen is exogenous to the bacterium.

In still another aspect, the invention features an immunogenic composition comprising an incapacitated bacterium and a pharmaceutically acceptable excipient, where the incapacitated bacterium is produced by infection of a pathogenic bacterium with a lysis-defective bacteriophage.

In specific embodiments of each of the above aspects, the pathogenic bacterium is of a genus selected from the group consisting of *Mycobacteria, Staphylococci, Vibrio, Enterobacter, Enterococcus, Escherichia, Haemophilus, Neisseria, Pseudomonas, Shigella, Serratia, Salmonella, Streptococcus, Klebsiella* and *Yersinia*, and wherein the bacteriophage inhibits growth of the infecting bacteria. In further specific embodiments of each of the above aspects, the lysis-defective bacteriophage is Lys minus bacteriophage.

A feature of the invention is that it provides methods for producing an immunogenic bacterial whole cell composition which is incapacitated in a manner that maintains the immunogenicity or antigenicity of the bacterium, but does not allow for recovery of the bacterium and replication and infection in the host.

Another feature of the invention is to provide for methods and compositions to effect a protective immune response against bacterial infections, particularly infections by pathogenic bacteria.

One advantage of the invention is that the bacteria incapacitated by infection with Lys minus bacteriophages are not capable of recovering from bacteriostasis upon removal of free bacteriophage. Thus, the incapacitated bacterial vaccines are associated with a substantially reduced risk of causing disease in a vaccinated host compared to live attenuated vaccines.

Another advantage of the invention is that antigen against which an immune response is desired when produced in a phage-incapacitated bacteria is not significantly modified in terms of the antigens presented on the bacterial cell surface or in terms of antigens that are provided as inclusion or aggregate bodies inside bacteria which are processed by the immune system, e.g., following phagocytosis of the bacterium by a macrophage. In contrast, chemically-induced bacterial inactivation can result in cross-linking of surface proteins and irreversible chemical modification of the antigen.

These and other objects, advantages, and features of the invention will become apparent to those persons skilled in the art upon reading the details of the compositions of the invention and their methods of use as more fully described below.

Lane 2: GMB2/GMB5 primers; Lane 3: marker; Lane 4: GMB5/GMB6 primers).

Figure 4:
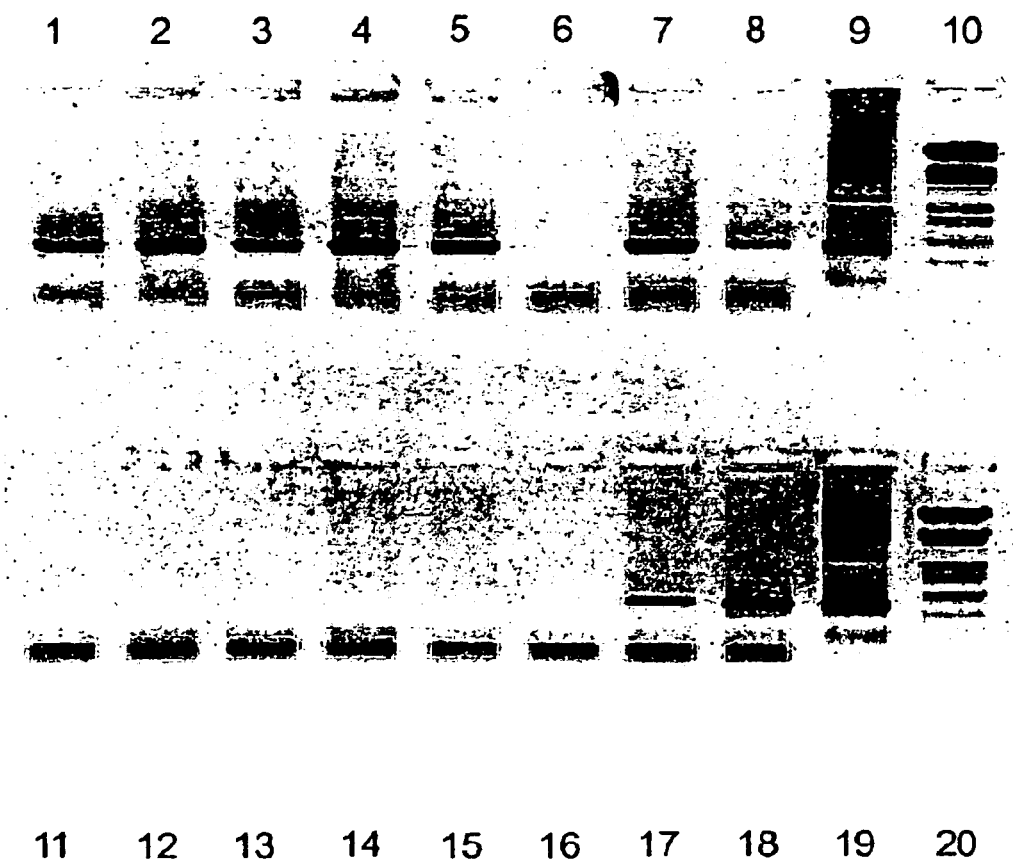

FIG. 4 illustrates PCR of turbid plaques for GFP gene product (Lanes 1–5, 7, 8, 17 & 18: pools positive for GFP gene product; Lanes 6, 11–16: pools negative for GFP gene product; Lanes 9, 19: positive control; Lanes 10, 20: MW marker).

Figure 5:
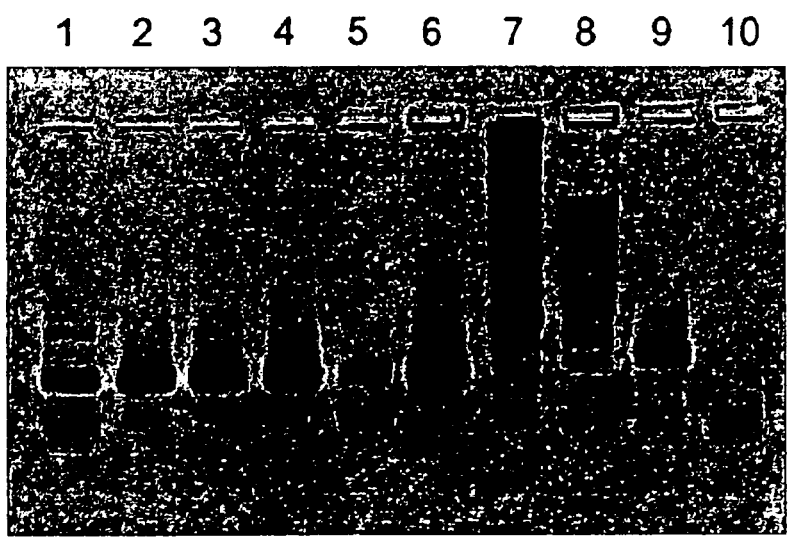

FIG. 5 depicts PCR of turbid plaques for Lysin-GFP-Lysin gene product (Lanes 1–6: turbid plaques #1, 2, 3, 4, 7, 8; Lane 7: positive control for Lysin-GFP-Lysin product (plasmid DNA); Lane 8: MW marker; Lane 9: positive control for lysin product (plasmid DNA); Lane 10: negative control).

Figure 6:
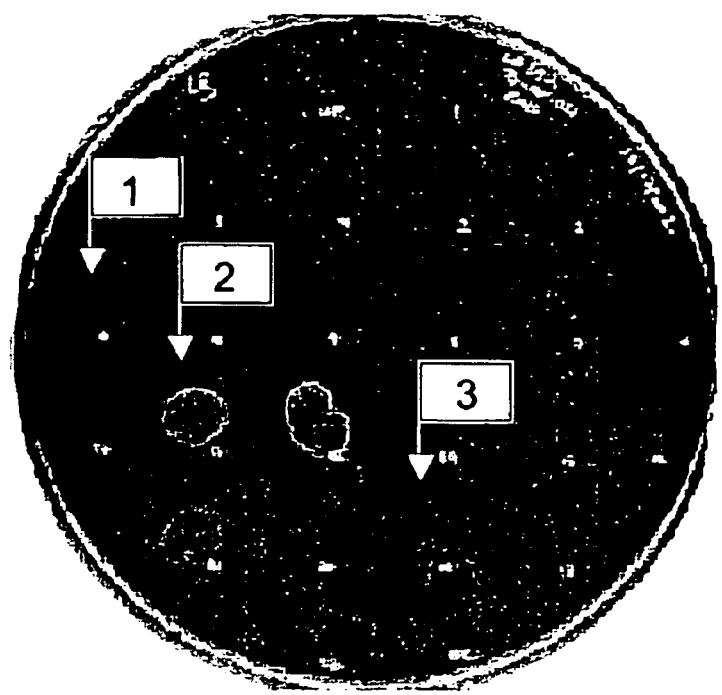

FIG. 6 illustrates recombinant phage lysates spotted on a lawn of E. coli showing different levels of contamination with wild phage or total absence of wild plaques (Spot #1: lysate #11 which shows a countable number of wild plaques; Spot #2: lysate which shows high number of wild plaques which completely lysed the cells; Spot #3: lysate which does not show any wild plaques).

Figure 7:
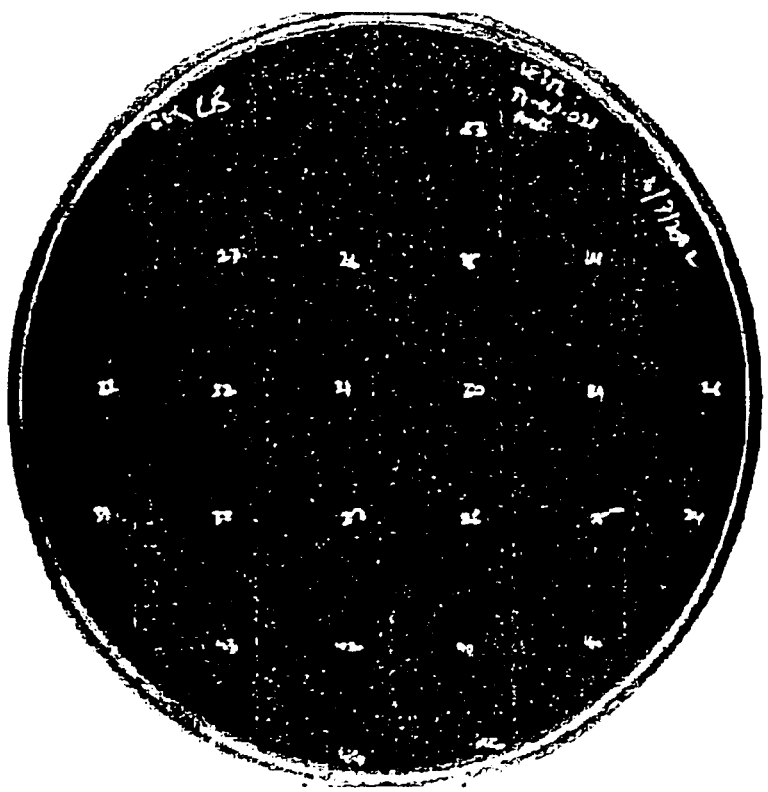

FIG. 7 illustrates recombinant phage containing lysates spotted on a lawn of E. coli showing absence of plaques.

Figure 8:
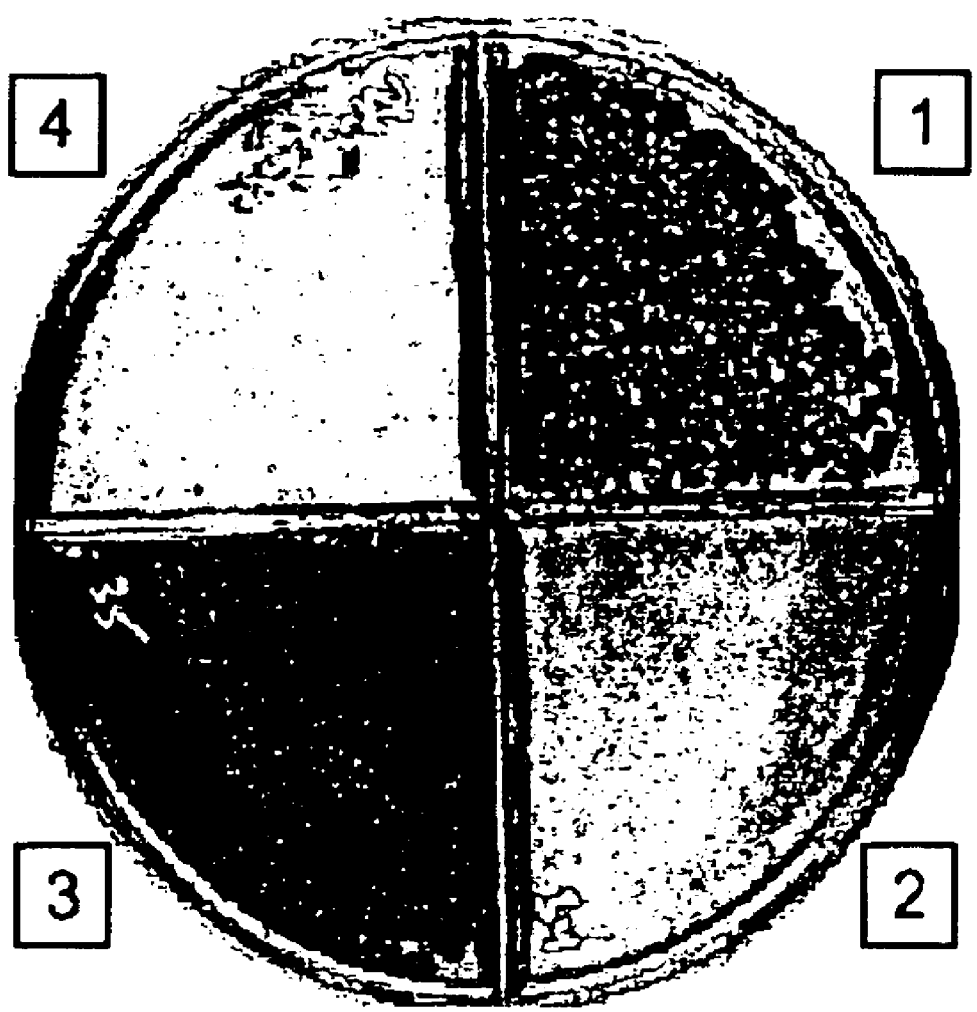

FIG. 8 illustrates recombinant phage (RP)-containing lysates leading to loss of viability of E. coli cells infected (Quadrant #1:50% loss of viability seen with RP-lysate #33; Quadrants #2 & 4: total loss of viability in case of RP-lysates #34 & #36; Quadrant #3: no significant loss of viability with RP-lysate #35).

Before the present invention is described, it is to be understood that this invention is not limited to particular methodology, protocols, bacteriophage, bacterial pathogens, animal species or genera, constructs, and reagents described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a bacteriophage" includes a plurality of such bacteriophage and reference to "the host cell" includes reference to one or more host cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides methods and compositions for production of inactivated whole cell bacteria, which bacteria are generated using bacteriophage defective in the ability to lyse the bacterial host cell. Bacteriophages are highly specific viruses that infect bacteria. Following infection of a bacterium like E. coli by a lytic phage, such as T4, a profound rearrangement of all macromolecular syntheses occurs. The RNA Polymerase (RNAP) of the host bacterium binds to the initiation sites of the phage genome known as Immediate-Early (IE) genes and transcribes them. Some of the IE gene products degrade the host(bacterial) DNA which lacks the modified base Hydroxy Methyl Cytosine (HMC) while another product ADP-Ribose, binds to the alpha subunits of the bacterial RNAP and renders it incapable of recognizing bacterial cell promoters. This results in the cessation of transcription of host genes. These events occur in the first 3 to 5 minutes after infection.

In the next stage, the modified RNAP recognizes and binds to the so-called Delayed Early (DE) genes, thus eliminating further expression of the IE genes of the phage. The DE gene products are involved in replicating the phage genome using the degraded bacterial DNA bases. One of the products of the DE genes is a novel sigma factor that causes the host RNAP to recognize only the Late (L) genes which are the next to be transcribed. The Late genes are involved in synthesizing new capsid proteins, tails and tail fibers and assembly proteins all of which are needed to assemble progeny phage particles. Finally, the phage lysozyme gene is activated resulting in the lysis of the bacterial host cell and release of the progeny phage.

During the past decade, the key components essential for host lysis by bacteriophages have been investigated. It is now recognized that two proteins, an endolysin and a holin are needed for host lysis to occur. Endolysins are muralytic enzymes that accumulate in the cytosol and holins are small membrane proteins that regulate access of the endolysins to the cell wall through the cytoplasmic membrane (Wang et al. Ann. Rev. Microbiol. 54, 799–825 (2000)). The lysis gene region of bacteriophage lambda was cloned into a multicopy plasmid, pBH 20 under the transcriptional control of the lac operator and induction of this "lysis operon" led to lytic behavior parallel to that of bacteriophage infected cells (Garrett, J. et al. Mol. Gen. Genet. 182, 326(1981). The two lysis genes cph1 and cpl1 of the *Streptococcal pneumoniae* bacteriophage Cp-1, coding for holin and lysin respectively, have been cloned and expressed in E. coli (Martin et al. J. Bacteriol. 180, 210 (1998)). Expression of the Cph1 holin resulted in bacterial cell death but not lysis. Concomitant expression of both holin and lysin of phage Cp-1 in E. coli resulted in cell lysis. Furthermore, the cph1 gene was able to complement a lambda Sam mutation (carrying an amber mutation in the holin gene) in the nonsuppressing E. coli HB 101 strain to release phage progeny. Regulated expression of lambda phage lysis genes S and R causes dramatic lysis of both Vibrio cholerae and Salmonella enterica serovar Typhimurium cells (Jain et al. Infect Immun, 68, 986 (2000).

The present invention features bacteria that are incapacitated (e.g., are not able to replicate so as to support an infection in a host), which bacterial are incapacitated by infection with specific bacteriophage lacking one or more components of the phage lysis system. The modified phage enters the bacterial host, disrupts the macromolecular syntheses of the host, replicates itself but does not lyse the bacterial host. The phage-infected bacteria are incapacitated and cannot spread the infection, but retain the antigenic epitopes on the cell surface in an essentially native conformation and configuration or express the antigen as an inclusion body or aggregate form, which can then be processed by the immune system, e.g., following phagocytosis of the bacterium by a macrophage. The phage-infected bacteria have essentially the same immunogenicity as the live pathogen, and therefore elicit a protective immune response against the bacterial pathogen. The incapacitated bacteria of the invention are thus useful in, for example, eliciting an immune response against an antigen of interest, e.g., for production of antibodies in a non-human animal, as a whole cell bacterial vaccine, and the like.

Specific aspects of the invention will now be described in more detail.

Definitions

By "bacteriophage" and "phage", which terms are used interchangeably herein, is meant any of a variety of viruses that have a specific affinity for and infect bacteria. These thus include, coliphages, which infect Escherichia coli (e.g., lambda phage and the T even phages, T2, T4 and T6). Phages generally are composed of a protein coat or capsid enclosing the genetic material, DNA or RNA, that is injected into the bacterium upon infection. In the case of virulent phages all synthesis of host DNA, RNA and proteins ceases and the phage genome is used to direct the synthesis of phage nucleic acids and proteins using the host's transcriptional and translational apparatus. These phage components then self assemble to form new phage particles. The synthesis of a phage lysozyme leads to rupture of the bacterial cell wall releasing, typically 100–200 phage progeny. The temperate phages, such as lambda, may also show this lytic cycle when they infect a cell, but more frequently they induce lysogeny, in which the phage integrates into the bacterial host DNA to persist as a prophage. In general, the bacteriophage of interest in the invention are lytic phages rather than temperate phages.

By "Lys minus phage" or "Lys minus bacteriophage", which terms are used interchangeably herein, is meant a phage deficient in lysin protein. Lys minus bacteriophage are incapable of facilitating efficient lysis of the bacterial host since the enzymatic activity of the lysin of the phage is needed for enzymatic degradation of the peptidoglycan layer of the bacterial cell wall. Lys minus bacteriophage retain activity in infection of its appropriate bacterial host, destruction of the bacterial genome, and replication, which are sufficient to inhibit bacterial growth and replication. Lys minus phage include those generated by mutating or deleting the gene encoding the lysin of the phage lysis system. Lys minus phage encompasses phage defective in lysin due to deletion of all or a portion of the lysin-encoding nucleic acid so that no detectable lysin is produced, or a truncated form of lysin is produced which has decreased activity in facilitating lysis (e.g., the truncated lysin is ineffective in promoting efficient lysis of the bacterial host, or does not facilitate any detectable wild-type lysin-mediated lysis activity). Lys minus phage also include those in which a lysin-encoding nucleic acid is operably linked to an inducible promoter such that lysin production occurs in an amount effective to induce lysis only when in the presence of an agent which activates the inducible promoter. Preferably, the inducer agent is one that is not normally found in a host to be treated using the phage, e.g., the inducer is not an agent that is endogenous to a host to be treated.

Lys minus phage also include phage that produce modified lysin protein, which lysin is defective in promoting bacterial lysis due to the presence of one or more mutations. Such mutations include at least one, or any combination of one or more, nucleic acid deletions, substitutions, additions, or insertions which result in an alteration in the corresponding amino acid sequence of the encoded lysin protein. Thus, Lys minus phage generally encompass phage in which the lysin gene is completely or partially deleted for the lysin gene or otherwise modified (e.g., by addition, substitution, or replacement of coding nucleotides) to provide for decreased or substantially no expression of functional lysin. Lys minus phage may also be produced by inhibiting lysin function in a host through expression of interfering RNA (e.g., antisense), or production of inhibitory peptides in the host cell, which interfering RINA or inhibitory peptides may be produced by the those cell (e.g., from a genetically modified host bacterial cell) or from a phage-delivered nucleic acid. Exemplary lysin-deficient phage are described in commonly owned U.S. provisional application Ser. No. 60/325,803, filed Sep. 27, 2001, and in a commonly owned U.S. application co-pending U.S. application Ser. No. 10/259,197, entitled "Lysin-Deficient Bacteriophages Having Reduced Immunogenicity," filed on same date as the instant application, each of which applications are specifically incorporated by reference herein in their entirety.

By "incapacitated" in the context of an incapacitated bacterial cell produced according to the invention, is meant that the bacterial cell is in a state of irreversible bacteriostasis. While the bacterium retains its structure—and thus retains, for example, the immunogenicity, antigenicity, and/or receptor-ligand interactions associated with a wild-type bacterium—it is not capable of replicating due to the presence of an infecting phage with in the bacterial cell.

By "isolated" is meant that the material is at least 60%, by weight, free from the proteins and naturally-occurring organic molecules with which it is naturally associated. Preferably, the material is at least 75%, more preferably at least 90%, and most preferably at least 99%, by weight, the material of interest. "Isolated" thus encompasses preparations that are enriched for the desired material.

The terms "polynucleotide" and "nucleic acid", used interchangeably herein, refer to a polymeric forms of nucleotides of any length, either ribonucleotides or deoxynucleotides. Thus, these terms include, but are not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "polypeptide" and "protein", used interchangeably herein, refer to a polymeric form of amino acids of any length, which can include coded and non-coded amino acids, chemically or biochemically modified (e.g., post-translational modification such as glycosylation) or derivatized amino acids, polymeric polypeptides, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The term "recombinant polynucleotide" as used herein intends a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

"Recombinant host cells", "host cells", "cells", "cell lines", "cell cultures", and other such terms denoting microorganisms or higher eukaryotic cells cultured as unicellular entities refer to cells which can be, or have been, used as recipients for recombinant vector or other transfer DNA, and include the progeny of the original cell which has been transfected. It is understood that the progeny of a single parental cell may not necessarily be completely identical in morphology or in genomic or total DNA complement as the original parent, due to natural, accidental, or deliberate mutation.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

An "open reading frame" (ORF) is a region of a polynucleotide sequence which encodes a polypeptide; this region may represent a portion of a coding sequence or a total coding sequence.

A "coding sequence" is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, and recombinant polynucleotide sequences.

"Heterologous" means that the materials are derived from different sources (e.g., from different genes, different species, etc.).

"Transformation", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host genome.

The terms "individual," "subject," "host," and "patient," are used interchangeably herein and refer to any subject having a bacterial infection amenable to treatment using the therapeutic bacteriophage of the invention, and for whom treatment or therapy is desired. Mammalian subjects and patients, particularly human subjects or patients are of particular interest. Other subjects may include cattle, dogs, cats, guinea pigs, rabbits, rats, mice, horses, and so on.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease.

"Treatment" as used herein covers any treatment of a disease in a subject, particularly a mammalian subject, more particularly a human, and includes: (a) preventing the disease or symptom from occurring in a subject which may be predisposed to the disease or symptom but has not yet been diagnosed as having it; (b) inhibiting the disease symptom, i.e., arresting its development; or relieving the disease symptom, i.e., causing regression of the disease or symptom.

By "infecting bacterium" is meant a bacterium that has established infection in the host, and which may be associated with a disease or undesirable symptom as a result. Generally, infecting bacteria are pathogenic bacteria.

By "drug-resistant bacteria" or "antibiotic-resistant bacteria" is meant a bacterial strain that is resistant to growth inhibition or killing by an antibiotic. Multi-drug resistant bacteria are resistant to two or more antibiotics. Drug resistance can encompass, for example, ineffective killing of the infecting bacteria such that at least an infectious dose remains in the subject and the infection continues, resulting in continued symptoms of the associated infectious disease or later evidence of such symptoms. Drug resistance can also encompass inhibiting growth of the drug-resistant bacteria until such time therapy is discontinued, after which the bacteria begin to replicate and further the infectious disease.

By "inhibition of bacterial growth" in the context of infection of a bacterial cell with a Lys minus bacteriophage is meant that, following infection of the bacteria, the bacteriophage inhibits or interferes with the bacterial host cell's normal transcriptional and/or translational mechanisms such that the infected bacteria does not undergo substantial cell division (replication) and is caused to enter a state of bacteriostasis.

The term "protective immunity" means that a vaccine, immunogenic composition or immunization schedule that is administered to a mammal induces an immune response that prevents, retards the development of, or reduces the severity of a disease that is caused by a pathogenic bacterium or diminishes or altogether eliminates the symptoms of the disease.

The phrase "in a sufficient amount to elicit an immune response to epitopes present in said preparation" means that there is a detectable difference between an immune response indicator measured before and after administration of a particular vaccine preparation or immunogenic composition. Immune response indicators include but are not limited to: antibody titer or specificity, as detected by an assay such as enzyme-linked immunoassay (ELISA), bactericidal assay, flow cytometry, immunoprecipitation, Ouchter-Lowny immunodiffusion; binding detection assays of, for example, spot, Western blot or antigen arrays; cytotoxicity assays, etc.

The terms "immunogenic bacterial composition", "immunogenic composition", and "vaccine" are used interchangeably herein to mean a preparation capable of eliciting a cellular and/or humoral immune response in a subject when administered in a sufficient amount to elicit an immune response to epitopes present in said preparation.

A "surface antigen" is an antigen that is present in a surface structure of a bacterial cell (e.g. the outer membrane, inner membrane, periplasmic space, capsule, pili, etc.).

The term "immunologically naïve" with respect to a particular bacterial pathogen denotes an individual (e.g., a mammal such as a human patient) that has never been exposed (through infection or administration) to the specific bacterial pathogen or to an antigen composition derived from such bacteria in sufficient amounts to elicit protective immunity, or if exposed, failed to mount a protective immune response.

As used herein, the term "antibody" refers to a polypeptide or group of polypeptides which are comprised of at least one antibody combining site. An "antibody combining site" or "binding domain" is formed from the folding of variable domains of an antibody molecule(s) to form three-dimensional binding spaces with an internal surface shape and charge distribution complementary to the features of an epitope of an antigen, which allows an immunological reaction with the antigen. An antibody combining site may be formed from a heavy and/or a light chain domain ($V_H$ and $V_L$, respectively), which form hypervariable loops which contribute to antigen binding. The term "antibody" includes, for example, vertebrate antibodies, hybrid antibodies, chimeric antibodies, altered antibodies, univalent antibodies, the Fab proteins, and single domain antibodies. An "anti-idiotype" antibody refers to a type of antibody which mimics the structure of an antigen to which another antibody is specific.

Bacteriophage for Production of Lys Minus Bacteriophage for Use in Production of Incapacitated Bacterial Vaccines A Lys minus phage useful in production of incapacitated bacteria, which in turn are useful in vaccines of the invention, can be generated from any wild-type bacteriophage, preferably from a lytic phage. Thus, the methods and compositions of the invention can be applied to the development of any of a variety of Lys minus bacteriophages which are specific for any of a variety of bacteria, and thus useful in the treatment of a wide variety of bacterial infection. While it is contemplated that the present invention can be used to generate any of a variety of whole cell bacterial vaccines, which vaccines can be used prophylactically or therapeutically, and either alone or in conjunction with other therapies (adjunctive or stand-alone) for bacterial infections.

Of particular interest is the development of vaccines for clinically-important bacterial species and strains, particularly drug-resistant bacterial species and strains. Examples of such are listed below. The American Type Culture Collection (ATCC, Manassas, Md.) accession number for an exemplary wild-type bacteriophage infecting the corresponding clinically-relevant strains are provided following the strain it infects. Such phage are exemplary of those that can be modified to be Lys minus to provide bacteriophage according to the invention. The list is as follows:

1. All clinically important members of the family Enterobacteriaceae, including, but not limited to:
   a. All clinically important strains of *Escherichia*, with *E. coli* being of particular interest (ATCC phage #23723-B2);
   b. All clinically important strains of *Klebsiella*, with *K. pneumoniae* (ATCC phage #23356-B 1) being of particular interest;
   c. All clinically important strains of *Shigella*, with *S. dysenteriae* being of particular interest (ATCC phage #11456a-B1);
   d. All clinically important strains of *Salmonella*, including *S. abortus-equi* (ATCC phage #9842-B1), *S. typhi* (ATCC phage #19937-B1), *S. typhimurium* (ATCC phage #19585-B1), *S. newport* (ATCC phage #27869-B1), *S. paratyphi-A* (ATCC phage #12176-B1), *S. paratyphi-B* (ATCC phage #19940-B1), *S. potsdam* (ATCC phage #25957-B2), and *S. pollurum* (ATCC phage #19945-B1);
   e. All clinically important strains of *Serratia*, most notably *S. marcescens* (ATCC phage #14764-B 1)
   f. All clinically important strains of *Yersinia*, most notably *Y. pestis* (ATCC phage #11953-B1)
   g. All clinically important strains of *Enterobacter*, most notably *E. cloacae* (ATCC phage #23355-B1);
2. All clinically important Enterococci, most notably *E. faecalis* (ATCC phage #19948-B1) and *E. faecium* (ATCC phage #19953-B1)
3. All clinically important *Haemophilus* strains, most notably *H. influenzae* (exemplary phage can be obtained from the World Health Organization (WHO) or other labs that make them available publicly);
4. All clinically important *Mycobacteria*, most notably *M. tuberculosis* (ATCC phage #25618-B1), *M. avium-intracellulare, M. bovis,* and *M. leprae.* (exemplary phage available commercially from WHO, via The National Institute of Public Healthy & Environmental Protection, Bilthoven, The Netherlands);
5. *Neisseria gonorrhoeae* and *N. meningitidis* (exemplary phage can be obtained publicly from WHO or other sources);
6. All clinically important *Pseudomonads*, with *P. aeuruginosa* being of particular interest (ATCC phage #14203-B1);
7. All clinically important *Staphylococci*, with *S. aureus* (ATCC phage #27690-B1) and *S. epidermidis* (exemplary phage available publicly through the WHO, via the Colindale Institute in London) being of particular interest;
8. All clinically important Streptococci, with *S. pneumoniae* being of particular interest (exemplary phage can be obtained publicly from WHO or other sources); and
9. *Vibrio cholera* (phage #14100-B1)

Additional bacterial pathogens, far too numerous to mention here, particularly those in which drug-resistance has developed, can also be susceptible to therapy according to the present invention. In short, all bacterial infections caused by bacteria for which there is a corresponding phage either currently available or for which phage can be identified, can be treated using the present invention by rendering the corresponding phage Lys minus, and contacting the bacteria with the Lys minus phage.

Novel phage can also be used in the present invention. Such novel phages are continuously isolated from hospital sewage and other sources by standard procedures. Typically, 9 ml of the sewage sample is mixed with 1 ml of 10×LB broth, 0.1 ml of overnight LB broth shake culture growth of target bacterial strain is added and incubated overnight at 37° C. Chloroform (0.1 ml) is added and incubated at 37° C. for 15 minutes with shaking at 300 rpm. This is then centrifuged at 14,000 rpm for 20 minutes at 4° C. and the supernatant is stored in sterile Eppendorf tubes. These crude phage preparations are further purified and characterized as needed.

Phage Lysins

Lysis of the host bacterial cell by many types of bacteriophages depends on at least two different sets of proteins (Young et al. Microbiol. Rev. 56, 430 (1992)). Degradation of the bacterial cell wall is accomplished by the lysins. The best studied examples are the T4 e gene product, a lysozyme (Tsugita et al. J. Biol. Chem. 243, 391 (1968)) and the lambda R protein, a transglycosylase (Garrett et al. Mol. Gen. Genet. 182, 326 (1981)). The lysin genes of a large number of bacteriophages have been identified and characterized in the past decade. These include the lysins of bacteriophage T7 (Inouye et al. Biol. Chem. 248, 7247 (1973), gp 19 from *Salmonella typhimurium* phage P22 (Rennell et al. Virol. 143, 280(1985), phi 29 gp 15 from two phages of the gram-positive bacteria *Lactococcus lactis* and *Bacillus subtilis* (Garvey et al. Nucleic Acids Res. 14, 10001 (1986)), the Pneumococcal bacteriophage Cp-1 (Garcia et al.

J. Virol. 61, 2573 (1987)), the Pseudomonas phage f6 (Caldentey et al. Biochim. Biophys. Acta 1159, 44 (1992)), the K gene of bacteriophage P2 (Ziermann et al. J. Bacteriol. 176, 4974 (1994)), gene 17 of bacteriophage P1 (Schmidt et al. Bacteriol. 178, 1099 (1996)), the *Listeria monocytogenes* bacteriophage lysins Ply 511 and Ply 518 (Gaeng et al. Appl. Environ. Microbiol. 66, 2951 (2000)) as well as numerous phages infecting Lactobacilli (Shearman et al. Appl. Environ. Microbiol. 60, 3063 (1994)); Henrich et al. J. Bacteriol. 177, 723 (1995)).

Additional phage lysins reported in the literature are given below.

Ackermann (1998) Tailed bacteriophages: the order caudovirales. *Adv Virus Res*, 51:135–201.

Arendt et al. (1994) Molecular characterization of lactococcal bacteriophage Tuc2009 and identification and analysis of genes encoding lysin, a putative holin, and two structural proteins. *Appl Environ Microbiol*, 60: 1875–1883.

Auad et al. (1999) Physical mapping and partial genetic characterization of the *Lactobacillus delbrueckii* subsp. *bulgaricus* bacteriophage 1b539. *Arch Virol*, 144: 1503–1512.

Boizet et al. (1990) Cloning, expression and sequence analysis of an endolysin-encoding gene of *Lactobacillus bulgaricus* bacteriophage mv1. *Gene*, 94: 61–67.

Calandra et al. (1980) Lysis and protoplast formation of group B streptococci by mutanolysin. *Infect Immun*, 28: 1033–1037.

Calandra et al. (1975) Cellular streptolysin S-related hemolysins of group A *Streptococcus* C203S. *Infect Immun*, 12: 13–28.

Chandry et al. (1997) Analysis of the DNA sequence, gene expression, origin of replication and modular structure of the *Lactococcus lactis* lytic bacteriophage sk1. *Mol Microbiol*, 26: 49–64.

Cohen et al. (1975) Simple procedure for production by group C streptococci of phage-associated lysin active against group A streptococci. *Appl Microbiol*, 29: 175–178.

Coleman et al. (1986) Cloning and expression in *Escherichia coli* and *Staphylococcus aureus* of the beta-lysin determinant from *Staphylococcus aureus*: evidence that bacteriophage conversion of beta-lysin activity is caused by insertional inactivation of the beta-lysin determinant. *Microb Pathog*, 1: 549–564.

Coleman et al. (1989) *Staphylococcus aureus* bacteriophages mediating the simultaneous lysogenic conversion of beta-lysin, staphylokinase and enterotoxin A: molecular mechanism of triple conversion. *J Gen Microbiol*, 135: 1679–1697.

Cooney et al. (1988) Molecular cloning and genetic analysis of the determinant for gamma-lysin, a two-component toxin of *Staphylococcus aureus*. *J Gen Microbiol*, 134:2179–2188.

de Ruyter et al. (1997) Food-grade controlled lysis of *Lactococcus lactis* for accelerated cheese ripening. *Nat Biotechnol*, 15: 976–979.

Diaz et al. (1996) The two-step lysis system of pneumococcal bacteriophage EJ-1 is functional in gram-negative bacteria: triggering of the major pneumococcal autolysin in *Escherichia coli*. *Mol Microbiol*, 19: 667–681.

Dietrich et al. (1998) Delivery of antigen-encoding plasmid DNA into the cytosol of macrophages by attenuated suicide *Listeria monocytogenes*. *Nat Biotechnol*, 16: 181–185.

Elias et al. (1980) *Staphylococcus aureus* haemolysins: their use in strain typing. *Acta Microbiol Acad Sci Hung*, 27: 183–190.

Fischetti et al. (1971) Purification and physical properties of group C streptococcal phage-associated lysin. *J Exp Med*, 133: 1105–1117.

Garcia et al. (1987) Cloning, purification, and biochemical characterization of the pneumococcal bacteriophage Cp-1 lysin. *J Virol*, 61: 2573–2580.

Garcia et al. (1983) Mechanism of phage-induced lysis in pneumococci. *J Gen Microbiol*, 129: 479–487.

Garcia et al. (1984) Biochemical characterization of a murein hydrolase induced by bacteriophage Dp-1 in *Streptococcus pneumoniae*: comparative study between bacteriophage-associated lysin and the host amidase. *J Bacteriol*, 159: 793–796.

Gindreau et al. (1999) Molecular analysis of the region encoding the lytic system from *Oenococcus oeni* temperate bacteriophage phi 10MC. *FEMS Microbiol Lett*, 171: 31–238.

Henrich et al. (1995) Primary structure and functional analysis of the lysis genes of *Lactobacillus gasseri* bacteriophage phi adh. *J Bacteriol*, 177: 723–732.

Hill et al. (1981) Identification of a lysin associated with a bacteriophage (A25) virulent for group A streptococci. *J Bacteriol*, 145: 696–703.

Kaneko et al. (1998) Complete nucleotide sequence and molecular characterization of the temperate staphylococcal bacteriophage phiPVL carrying Panton-Valentine leukocidin genes. *Gene*, 215:57–67.

Kuhnemund (1972) Studies on the lysis of *streptococcus pyogenes* (group A, type 1) by phage-associated lysin (author's transl). *Z Immunitatsforsch Exp Klin Immunol*, 143:184–191.

Loessner et al. (1996) Modified *Listeria* bacteriophage lysin genes (ply) allow efficient overexpression and one-step purification of biochemically active fusion proteins. *Appl Environ Microbiol*, 62: 3057–3060.

Loessner et al. (1995) Heterogeneous endolysins in *Listeria monocytogenes* bacteriophages: a new class of enzymes and evidence for conserved holin genes within the siphoviral lysis cassettes. *Mol Microbiol*, 16: 1231–1241.

Martin et al. (1998) Functional analysis of the two-gene lysis system of the pneumococcal phage Cp-1 in homologous and heterologous host cells. *J Bacteriol*, 180:210–217.

Mindich et al. (1979) Cell wall lysin as a component of the bacteriophage phi 6 virion. *J Virol*, 30: 489–496.

Mullan et al. (1985) Lysin production by phi C2(W), a prolate phage for *Streptococcus lactis* C2. *J Dairy Res*, 52: 113–121.

Mullan et al. (1985) Partial purification and some properties of phi C2(W) lysin, a lytic enzyme produced by phage-infected cells of *Streptococcus lactis* C2. *J Dairy Res*, 52:123–138.

Nelson et al. (2001) Prevention and elimination of upper respiratory colonization of mice by group A streptococci by using a bacteriophage lytic enzyme. *Proc Natl Acad Sci USA*, 98: 4107–4112.

Oki et al. (1996) Cloning, sequence analysis, and expression of the genes encoding lytic functions of Bacteriophage phi g1e. *Gene*, 176: 215–223.

Payne et al. (1996) Exploitation of a chromosomally integrated lactose operon for controlled gene expression in *Lactococcus lactis*. *FEMS Microbiol Lett*, 136: 19–24.

Raina (1981) Purification of *Streptococcus* group C bacteriophage lysin. *J Bacteriol*, 145: 661–663.

Sable et al. (1995) The lysins of bacteriophages infecting lactic acid bacteria. *Appl Microbiol Biotechnol*, 43: 1–6.

Sanders et al. (1997) A chloride-inducible gene expression cassette and its use in induced lysis of *Lactococcus lactis*. *Appl Environ Microbiol*, 63: 4877–4882.

Shearman et al. (1989) Cloning and DNA sequence analysis of a *Lactococcus* bacteriophage lysin gene. *Mol Gen Genet*, 218: 214–221.

Shearman et al. (1994) Controlled expression and structural organization of a *Lactococcus lactis* bacteriophage lysin encoded by two overlapping genes. *Appl Environ Microbiol*, 60: 3063–3073.

Sheehan et al. (1996) Analysis of the catalytic domain of the lysin of the lactococcal bacteriophage Tuc2009 by chimeric gene assembling. *FEMS Microbiol Lett*, 140: 23–28.

Sheehan et al. (1997) The lytic enzyme of the pneumococcal phage Dp-1: a chimeric lysin of intergeneric origin. *Mol Microbiol*, 25: 717–725.

Sheehan et al. (1999) Identification and characterization of a lysis module present in a large proportion of bacteriophages infecting *Streptococcus thermophilus*. *Appl Environ Microbiol*, 65: 569–577.

Sonstein et al. (1971) Staphylococcal bacteriophage-associated lysin: a lytic agent active against *Staphylococcus aureus*. *J Bacteriol*, 107: 499–504.

Tourville et al. (1966) Lactic streptococcal phage-associated lysin. I. Lysis of heterologous lactic streptococci by a phage-induced lysin. *J Dairy Sci*, 49: 158–162.

van der Vijver et al. (1975) Induction of mutation in *Staphylococcus aureus* by ethylmethane sulphonate. *J Med Microbiol*, 8: 265–277.

van Sinderen et al. (1996) Sequence analysis and molecular characterization of the temperate lactococcal bacteriophage r1t. *Mol Microbiol*, 19: 1343–1355.

Ward et al. (1993) Sequence analysis of the lysin gene region of the prolate lactococcal bacteriophage c2. *Can J Microbiol*, 39: 767–774.

Wheeler et al. (1980) Production of group C streptococcus phage-associated lysin and the preparation of *Streptococcus pyogenes* protoplast membranes. *J Gen Microbiol*, 120:27–33.

Yoon et al. (2001) Characterization of a lytic *Lactobacillus plantarum* bacteriophage and molecular cloning of a lysin gene in *Escherichia coli*. *Int J Food Microbiol*, 65: 63–74.

Young (1992) Bacteriophage lysis: mechanism and regulation. *Microbiol Rev*, 56:430–481.

Where the lysin gene of a bacteriophage of interest has not yet been identified, such identification can be accomplished using methods routine in the art. Bacteriophage lysin genes can be identified by, for example, methods based upon sequencing of the bacteriophage genome, and comparison of the sequence to those of bacteriophage in which the lysin gene has been described. Comparison of the amino acid sequences of the lysins described to date reveals three conserved regions (Schmidt et al. J. Bacteriol. 178, 1099 (1996). The first conserved region contains the catalytic site with the EG sequence and the active-site cleft. The lysin genes of newly isolated bacteriophages, or bacteriophages in which the lysin gene has not yet been described, can be identified and isolated by nucleic acid amplification techniques (e.g., PCR) using primers corresponding to the nucleotide sequences from the conserved regions of known lysin genes. Using conserved parts of the lysin gene, the lysin genes from any phage can be isolated, using degenerate oligos homologous to any two of the three conserved regions. Once this PCR product is sequenced, new primers can be designed to sequence the regions upstream and downstream of the lysin genes, using phage DNA as template for sequencing.

Generation of Mutant Lys Minus Phages

Lys minus phage can be generated in any of a variety of ways consistent with providing a lysis-defective phage according to the invention. Preferably Lys minus phage are generated by modifying the bacteriophage genome so that the bacteriophage is deficient in wild-type lysin (Lys) protein or so that the bacteriophage contains a functional lysin gene operably linked to an inducible promoter. Alternatively, bacteriophage have reduced levels of lysin, and thus reduced lysis rates, can be selected by screening for phage that infect bacteria and inhibit replication of the bacterial host, but which have reduced rates of lysis, e.g., the bacteriophage acts as bacteriostatic agent of the bacterial host, but does not lyse the bacterial host cell at a rate or level associated with a wild-type phage that is not deficient in the phage lysis system.

Bacteriophage deficient in the lysin protein ("Lys minus" phage), include those generated by mutating or deleting the gene encoding the lysin of the phage lysis system. "Lys minus" phage encompasses phage defective in lysin due to deletion of all or a portion of the lysin-encoding nucleic acid so that no detectable lysin is produced, or a truncated form of lysin is produced which has decreased activity in facilitating lysis (e.g., the truncated lysin is ineffective in promoting efficient lysis of the bacterial host, or does not facilitate any detectable wild-type lysin-mediated lysis activity). "Lys minus" phage also include phage that produce modified lysin protein, which lysin is defective in promoting bacterial lysis due to the presence of one or more mutations. Such mutations include at least one, or any combination of one or more, nucleic acid deletions, substitutions, additions, or insertions which result in an alteration in the corresponding amino acid sequence of the encoded lysin protein.

Lys minus phage also include those in which the gene encoding lysin has been modified such that the gene is operably linked to an inducible promoter so that lysin is only produced when the phage is either contacted with an agent or an environmental condition (such as temperature, metals, salts, ions, nutrients, drugs, etc) that activates the inducible promoter. Such Lys minus phage can be produced by modifying the wild-type lysin gene to include an inducible promoter, by replacing the lysin gene with a lysin-encoding nucleic acid operably linked to an inducible promoter; or by mutating or deleting the gene encoding lysin and inserting into the phage a lysin-encoding nucleic acid operably linked to an inducible promoter.

Bacteriophage having defective lysin can be generated using classical microbiological methods, such as plaque morphology assays (see, e.g., Streisinger et al. Cold Spring Harbor Symp. Quant. Biol. 26, 25 (1961)).

Lys minus phage can also be generated using recombinant techniques, such as site-directed mutagenesis (Smith Ann. Rev. Genet. 19, 423 (1985)), e.g., using nucleic acid amplification techniques such as PCR (Zhao et al. Methods Enzymol. 217, 218 (1993)) to introduce facile deletions, insertions and point mutations. Other methods for deletion mutagenesis involve, for example, the use of either BAL 31 nuclease, which progressively shortens a double-stranded DNA fragment from both the 5' and 3' ends, or exonuclease III, which digests the target DNA from the 3' end (see, e.g., Henikoff Gene 28, 351 (1984)). The extent of digestion in both cases is controlled by incubation time or the temperature of the reaction or both. Point mutations can be introduced by treatment with mutagens, such as sodium bisulfite, which deaminates deoxycytidine to deoxyuridine resulting in the substitution of an A:T base pair for a G:C base pair in approximately 50% of the template molecules after one round of replication (Botstein et al. Science 229, 1193 (1985)).

Other exemplary methods for introducing point mutations involve enzymatic incorporation of nucleotide analogs or misincorporation of normal nucleotides or alpha-thionucleotide by DNA polymerases (Shortle et al. Proc. Natl. Acad. Sci. USA 79, 1588 (1982)). In oligonucleotide-directed mutagenesis, the target DNA is cloned into an M13 vector to produce single-stranded wild-type DNA template to which the oligo mutagen is annealed. This produces a noncomplementary (looped out) region on the oligo primer or on the template, resulting in an insertion or a deletion, respectively. Base pair mismatch between the template and the primer results in point mutagenesis. PCR-based mutagenesis methods (or other mutagenesis methods based on nucleic acid amplification techniques), are generally preferred as they are simple and more rapid than classical techniques described above (Higuchi et al. Nucleic Acids Res. 16, 7351 (1988); Vallette et al. Nucleic Acids Res. 17, 723 (1989)).

Bacteriophage defective in lysin can be identified by screening candidate phage by, for example, comparing the ability of the candidate phage to lyse a wild-type bacterial host to the ability of the candidate phage to lyse a recombinant bacterial host modified to express the lysin protein (e.g., by a helper phage, from an introduced helper plasmid encoding the phage's lysin, or from a recombinant phage lysin-encoding sequence integrated in the bacterial host's genome). Candidate phage that lyse the lysin-expressing bacterial host, but that fail to effect, or do not efficiently effect, lysis of the wild-type bacterial host represent exemplary Lys minus phage suitable for use in the invention.

One approach of particular interest for generating Lys minus phages totally lacking the lysozyme activity of the lysin gene is to delete the first conserved region which contains the catalytic site and the active site cleft. Based on the nucleotide sequence of the lysin, PCR product(s) lacking the conserved region I are generated and transformed into the appropriate bacterial host together with the wild-type phage. A selectable marker, such as the jellyfish green fluorescent protein (GFP, Chalfie, M. et al. Science 263, 802, 1994), can be used instead of an antibiotic resistance marker. Antibiotic resistance markers may prove undesirable where the phage may be within the vaccine at some level (e.g., as a contaminant). Replicas of the resistance bacteria (to avoid UV mutagenesis) are then screened under UV light for those expressing GFP.

Production of Lys Minus Phages Using Marker Rescue Techniques

In another embodiment, Lys minus phage having a desired defect in the lysin gene are generated using marker rescue techniques. The technique of marker rescue has been used extensively to map mutations in phage, and to transfer artificially-generated mutations from phage genes cloned in a plasmid to the phage genome (Volker et al. Mol. Gen. Genet. 177, 447 (1980)). Exemplary of the use of this technique is the application to identify genes involved in T4 phage assembly and maturation. Specifically, restriction fragments containing the T4 phage assembly and maturation genes 20 to 22 were cloned in plasmids, mutagenized, and the mutations were then recombined back into the phage genome by infection of E. coli carrying the plasmid with a T4 20/21 am (amber) double mutant (Volker, supra, 1980). The phage progeny that had undergone recombination with the plasmid were selected by plating on a su⁻ host (lacking an amber suppressor) allowing the selection of recombinant phage. These am⁺ phages, were then screened non-selectively for the desired temperature-sensitive mutations in genes 20 and 21.

Figure 1:
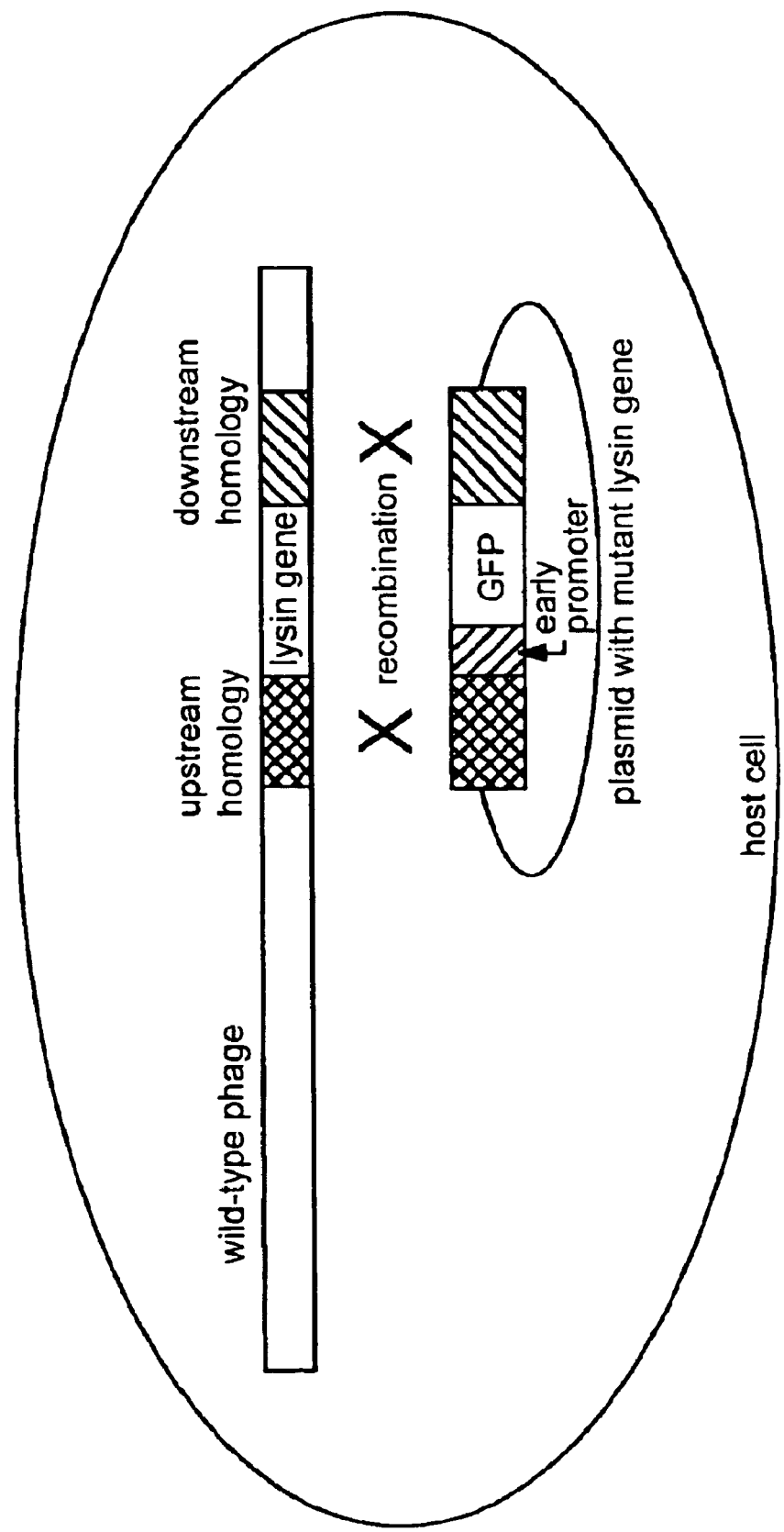
FIG. 1 is a schematic showing the use of a bacterial host having a plasmid with a mutant lysin gene for use in production of Lys minus bacteriophage of the invention.

A similar strategy can be employed for the lysin gene. The mutant lysin gene (either a non-functional lysin gene or a functional lysin gene operably linked to an inducible promoter), which can be generated using recombinant techniques described above, is cloned into a plasmid having a selectable marker, e.g., ampicillin-resistance. Two types of bacterial hosts containing plasmids with either wild-type (WT lysin host) or mutant lysin genes (mutant lysin host) are used. The former strain containing the wild type lysin gene is used as the helper strain for large scale production of mutant Lys minus phage, where the Lys– minus phage is one lacking an inducible lysin gene. The latter strain containing the mutant lysin gene is used to introduce Lys⁻ mutations in wild-type phage. FIG. 1 provides a schematic of a bacterial host cell having a mutant lysin gene useful in generating Lys minus phage of the invention.

Recombinant, mutant lysin-expressing bacterial hosts for production of Lys minus phages (as illustrated in FIG. 1) can be generated by using methods well known in the art. For example, the sequences of the regions flanking the lysin gene (about 100 bp on each side) in each of the phages to be mutated are isolated. Generally, at least about 50 bp homology is provided on each side, flanking the region of interest encoding the phage lysin gene (Singer (1982) Cell, 31: 25–33). The DNAs corresponding to the upstream and downstream regions of each phage lysin gene is isolated by nucleic acid amplification (e.g., PCR) and cloned into a plasmid having a first selectable marker (e.g., ampicillin resistance) with a suitable restriction site between two regions for insertion of a DNA cassette in which a second selectable marker (e.g., GFP) is expressed from an early promoter of the same phage. This plasmid is introduced into appropriate bacterial host cells by transformation and selection for the first selectable marker (exemplified here by ampicillin resistance). An exemplary plasmid with a mutant lysin gene useful in this technique is shown in FIG. 1. Alternatively, the construct of the plasmid may be genomically integrated in the bacterial host genomic DNA.

The bacterial host harboring the mutant lysin gene is infected with wild-type phage at a low multiplicity of infection. As the phage replicates, some of the phage recombine by a double crossover event with the mutant lysin gene in the bacterial host to yield Lys minus phage. Since it is likely that recombination in any cell will not be 100% efficient, there may be wild-type phage in the same cells as the Lys minus phage. The wild-type virus will act as helper virus to cause lysis of infected cells whether or not recombination occurs.

The two types of viruses are collected by lysing the bacterial cells with chloroform, and the Lys minus phage purified away from the wild-type virus by plaque purification. The virus from each plaque is then tested to see if it is wild-type or Lys minus. Testing to identify Lys minus phage can be accomplished by, for example, examining the ability of the phage from each plaque to infect and kill two types of host cells as detected by plaque formation. One type of host cell is the normal (wild-type) host bacterium, the other is the wild-type lysin host bacterium described above. Wild-type phage will effectively lyse and kill both types of hosts, while Lys minus phage kills only the host cells expressing lysin.

Where the Lys minus phage expresses a detectable marker (e.g., GFP), and particularly where the selectable marker is expressed from a viral early promoter, fluorescent plaques representing Lys minus phage can be visualized directly during plaque purification. The Lys minus phenotype of these phage can then be confirmed by screening as described above.

Generation of Wild-Type Lysin Host for Scale-Up Production of Lys Minus Phase

Lys minus phages can replicate and assemble in their host bacteria but, by definition, will not be able to lyse the host and release the progeny phages efficient. For the production of therapeutic Lys minus phages, release of the modified phages from the bacterial host is essential. Where the Lys minus phage is one in which a lysin gene is under control of an inducible promoter, lysis of the bacterial host can be accomplished by contacting the phage with an agent that activates the inducible promoter, thereby inducing lysin production and consequent lysis of the host bacteria cells.

Lysis of the host bacteria and release of the Lys minus phage can also be accomplished by introducing a helper plasmid carrying a lysin gene under an inducible promoter into the bacterial host. Previous studies have shown that expression of phage lambda lysis genes in *E. coli* results in a sharply defined lysis (Garrett et al. Mol. Gen. Genet. 182, 326, 1981). Recently, lambda phage S and R gene products (holin and lysin respectively) have been used in an inducible lysis system (Jain et al. Infection & Immunity 68, 986, 2000). Thus, large quantities of Lys minus phages can be produced in appropriate hosts containing a helper plasmid carrying a lysin gene coding for a highly potent lysozyme (e.g. T4 lysozyme) under an inducible promoter.

Lysin genes from any of the sequenced phages can be isolated by nucleic acid amplification techniques (e.g., PCR) and cloned in plasmid having a selectable marker (e.g., antibiotic resistance such as ampicillin resistance) so that they are expressed from an inducible promoter using standard recombinant DNA procedures. The lysin gene chosen will be one with the least amount of homology to the phage lysin gene to avoid recombination between the Lys minus phage and the lysin gene in the host strain to produce wild-type recombinants. The efficacy of production of only Lys minus phages is tested by confirming that the Lys minus phage stock does not produce plaques on a host strain lacking the lysin gene. If necessary, a variety of helper host strains expressing lysin from different sources and inducible promoters can be used to find empirically the appropriate host strain that yields the lowest level of wild-type recombinants.

Alternative Strategies for Production of Lysis-Defective Bacteriophages

Lysis-defective bacteriophages of the invention can also encompass not only phage that have a defective lysin gene, but also phage that are defective in the lysis machinery due to defects other than in the Lys gene or in addition to the Lys gene. For example, rather than being defective in only the lysin gene, both the lysin gene and the holin gene can be deleted or altered to be non-functional in the phage and the lysis system. Such defective phage can be produced by expressing the missing or defective lysis system components on a helper plasmid in the bacterial host. Martin et al (J. Bacteriol. 180, 210(1998) have shown that concomitant expression of both holin and lysin of the Pneumococcal phage Cp-1 in *E. coli* resulted in cell lysis. Similar strategies discussed above can be used to avoid generation of wild-type phage by recombination during the production phase.

Since the holins are the membrane-spanning proteins that allow phage lysins to access the bacterial cell wall murein, deletion or inactivation of the holin gene alone is also sufficient for generating therapeutic bacteriophages lacking immune response potential. Depending on the structure and properties of the specific phage, deletion or inactivation of either the lysin gene, the holin gene, or both could be employed to generate the desired therapeutic phage.

Any phage strain capable of facilitating direct or indirect harm to a bacteria (or other pathogen) (e.g., in inhibiting or interfering with transcription and/or translation of bacterial DNA (e.g., through competition of phage DNA for the same host cell machinery), inhibiting bacterial replication, and the like) is contemplated as useful in the present invention. Thus, phages that are lytic, and phages that are lysogenic but can later become lytic can be adapted for use in the present invention.

Bacterial Pathogens for Which Incapacitated Whole Cell Vaccines can be Generated According to the Invention Any of a variety of pathogenic bacteria can be used to generate an incapacitated, whole cell bacterial vaccine according to the invention. Exemplary bacterial pathogens are those described above along with their corresponding bacteriophages (where known).

In addition, the Lys minus bacteriophage can be used to create incapacitated whole cell bacterial vaccines using bacteria that are genetically engineered to express a heterologous protein or to overexpress an endogenous protein. For example, the bacterium can be genetically modified to express one or more nucleic acids that encode one or more molecules of interest, particularly molecules that elicit or enhance a protective immune response, e.g, recombinant antigens. Of particular interest are antigenic fragments of such molecules, e.g. epitopes. The nucleic acids may, for example, encode all or part of an outer membrane protein, pilin, flagellum, or other protein that is implicated in eliciting a protective immune response.

Any DNA sequence which encodes an antigenic molecule, or fragment thereof (e.g., epitope), from either a heterologous or endogenous organism, which when expressed in bacteria produces protective immunity against the organism or against a condition or disorder caused by the organism, can be isolated for use in the vaccine preparations of the present invention. In one embodiment, the antigen is a surface antigen. In another embodiment, the organism is a pathogenic microorganism. In yet another embodiment, the antigenic molecule, or fragment thereof, is characteristic of cancer and provides protective immunity against the cancer or elicits an immune response against the cancer resulting in reduction or elimination of the cancer from a subject.

Antigenic molecules, or fragments thereof, may be found on pathogens, such as bacteria, parasites, viruses or fungi. Bacteria, parasites, viruses and fungi of interest include, but are not limited, to those listed in the Table below.

| PARASITES: | BACTERIA: |
| --- | --- |
| Plasmodium spp. (e.g., *P. falciparum, P. vivax, P. ovale, P malariae*) | Vibrio spp. (e.g. *V. cholerae*) |
| | Neisseria spp. (e.g., *N menigitidis, N.gonorrhoeae*) |
| | *Corynebacteria diphtheriae* |
| Eimeria spp. | *Clostridium tetani* |
| Schistosoma spp. | *Branhamella catarrhalis* |
| Trypanosoma spp. | *Bordetella pertussis* |
| Babesia spp. | Haemophilus spp. (e.g., *H. influenzae*) |

-continued

| | |
|---|---|
| Leishmania spp. | Chlamydia spp. |
| Cryptosporidia spp. | Escherichia spp. (e.g., *E coli*) |
| Toxoplasma spp. | *Bacillus anthracis* |
| Pneumocystis spp.. | *Borrelia burgdorferi* |
| | Shigella spp. (e.g., *S. dysenteriae*) |
| | Pseudomona spp. (e.g., *P. aeruginosa*) |
| | Enterococcus spp. (e.g, *E. faecalis, E. faecium*) |
| | Streptococcus spp. (e.g., *S. pneumoniae*) |
| | Staphylococcus spp. (e.g., *S. aureus, S. epidermidis* |
| | Salmonella spp. (e.g., *S. abortus-equi, S. typhi, S. typhimurium, S. newport, S. paratyphi-A, S. paratyphi-B, S. potsdam,* and *S. pollurum*) |
| | Serratia spp. (e.g, *S. marcescens*) |
| | Klebsiella spp. (e.g., *K. pneumoniae*) |
| | Yersinia spp. (e.g., *Y. pestis*) |
| | Enterobacter spp. (e.g., *E. cloacae*) |
| | Serratia spp. |
| | Mycobacterium spp. (e.g., *M. tuberculosis, M. avium-intracellulare, M. bovis, M. leprae*) |
| | Rickettsia spp. (e.g., *R. prowazekii, R. typhi, R. rickettsii*) |
| | *Rochalimaea quintana* |
| | *Coxiella burnetii* |

| FUNGI: | VIRUSES: |
|---|---|
| Candida spp. (e.g., *C. albicans*) | Human Immunodeficiency virus, type I |
| | Human Immunodeficiency virus, type II |
| Cryptococcus spp. (e.g., *C. neoformans*) | Simian Immunodeficiency virus |
| | Human T lymphocyte virus, type I, II and III |
| Blastomyces spp. (e.g., *B. dermatitidis*) | Respiratory syncytial virus |
| | Hepatitis A virus |
| Histoplasma spp. (e.g., *H. capsulatum*) | Hepatitis B virus |
| | Hepatitis C virus |
| Coccidioides spp. (e.g., *C immitis*) | Non-A, Non-B Hepatitis Virus |
| | Herpes simplex virus, type I |
| Paracoccidioides spp. (e.g., *P. brasiliensis*) | Herpes simplex virus, type II |
| | Cytomegalovirus |
| Aspergillus spp. | Influenza virus |
| | Parainfluenza virus |
| | Poliovirus |
| | Poxvirus |
| | Rotavirus |
| | Coronavirus |
| | Rubella virus |
| | Measles virus |
| | Mumps virus |
| | Varicella |
| | Epstein Barr virus |
| | Adenovirus |
| | Papilloma virus |
| | Flaviviridae (e.g., yellow fever virus, dengue fever virus, Japanese encaphilitis virus) |

In addition, antigenic molecules of cancer cells can be used. Antigens characteristic of cancer cells and useful in the vaccine preparations of the present invention include, but are not limited to, MAGE, MUC1, HER2/neu, CEA, pS3, Tyrosinase, MART-1/melan A, gp 100, TRP-1, TRP-2, PSA, CDK4-R24C, BCR/ABL, Mutated K-ras, ESO-1, CA15-3, CA125, CA19-9, CA27.29, TPA, TPS, Cytokeratin 18, and Mutated p53.

Where antigens have not yet been identified, potentially useful antigens for vaccine formulations can be identified by various criteria, such as the antigen's involvement in neutralization of a pathogen's infectivity (Norrby, E., 1985, Summary, in Vaccines 85, Lerner, R. A., R. M. Chanock, and F. Brown (eds.), Cold Spring Harbor Laboratory, Cold Spring Harbor, N.Y., pp. 388–389), type or group specificity, recognition by patients' antisera or immune cells, and/or the demonstration of protective effects of antisera or immune cells specific for the antigen.

Immunoreactive molecules can be identified and characterized by methods known in the art. Monoclonal antibodies can be generated to the surface or other molecules of a pathogen to identify those that are capable of being recognized by the antibodies. Alternatively, small synthetic peptides conjugated to carrier molecules can be tested for generation of monoclonal antibodies that bind to the sites corresponding to the peptide on the intact molecule (see, e.g., Wilson, I. A., et al., 1984, Cell 37:767).

Genetically engineered bacteria useful in the invention can be created by employing recombinant DNA technology. A nucleotide sequence which encodes an antigenic molecule of interest is inserted into an expression vector, transformed or transfected into an appropriate bacterial host cell and cultivated under conditions suitable for expression. These procedures are well known in the art and are described generally in Sambrook, et al., Molecular Cloning, A Laboratory Manual, Cold Spring Harbor Press, Cold Spring Harbor, N.Y. (1989).

The nucleotide sequence encoding an antigenic molecule may also be fused to with a nucleic acid, bacterial or otherwise, to facilitate expression and/or, where desired, facilitate presentation of the expressed antigenic polypeptide on the bacterial cell surface (Cattozzo et al., J. Biotechnol 56, 191 (1997), Stocker and Newton, Int. Rev. Immunol. 11, 167 (1994), Stocker, Res. Microbiol. 141, 787 (1990), Newton et al., Science 244, 70 (1989), U.S. Pat. No. 6,130,082)). For example, Newton et al. (Res. Microbiol. 146, 203 (1995)) fused an HIVI gp41 epitope, which is part of the gp160 protein, to a *Salmonella* flagellum gene in correct orientation and reading frame. The plasmid was placed in a flagellin-negative live-vaccine *Salmonella* strain, which then made a protein with the foreign HIV1 epitope sequence integrated into it. Mice immunized with live-vaccine of the recombinant *Salmonella* showed production of antibody with affinity for gp160.

The nucleotide sequence encoding an antigenic molecule may also be fused to with a nucleic acid, bacterial or otherwise, to facilitate presentation of the expressed antigenic polypeptide on the cell surface of the genetically engineered bacteria (Cattozzo et al., J. Biotechnol 56, 191 (1997), Stocker and Newton, Int. Rev. Immunol. 11, 167 (1994), Stocker, Res. Microbiol. 141, 787 (1990), Newton et al., Science 244, 70 (1989), U.S. Pat. No. 6,130,082)). For example, Newton et al. (Res. Microbiol. 146, 203 (1995)) fused an HIV1 gp41 epitope, which is part of the gp160 protein, to a *Salmonella* flagellum gene in correct orientation and reading frame. The plasmid was placed in a flagellin-negative live-vaccine *Salmonella* strain, which then made a protein with the foreign HIV 1 epitope sequence integrated into it. Mice immunized with live-vaccine of the recombinant *Salmonella* showed production of antibody with affinity for gp160.

Immunopotency of the antigenic molecule expressed by the genetically engineered bacteria in an incapacitated, whole cell vaccine preparation, can be determined by monitoring the immune response of test animals following immunization with the bacteria expressing the recombinant antigen. Test animals may include mice, guinea pigs, rabbits, chickens, chimpanzees and other primates, and eventually human subjects. Methods of introduction of the incapacitated recombinant bacteria may include oral, intradermal, intramuscular, intraperitoneal, intravenous, subcutaneous, intranasal or any other standard routes of immunizations.

The immune response of the test subjects can be analyzed by various approaches such as: (a) the reactivity of the resultant immune serum to the native antigen or a fragment thereof, or to the isolated naturally occurring organism (e.g., wild-type organism) from which the test antigenic molecule was derived, as assayed by known techniques, e.g., enzyme linked immunosorbant assay (ELISA), immunoblots, radioimmunoprecipitations, etc., (b) the reactivity of lymphocytes isolated from the immunized subject to the native antigen or fragment thereof, or the naturally occurring organism from which the test antigenic molecule was derived, as assayed by known techniques, e.g., blastogenic response assays, cytotoxicity assays, delayed type hypersensitivity, etc., (c) the ability of the immune serum to neutralize infectivity of the organism in vitro or the biologic activity of the native antigen, and (d) protection from disease and/or mitigation of infectious symptoms in immunized animals.

Use of Inactivated Bacteria for Production of Antibodies

For the production of antibodies against an antigenic molecule expressed by bacteria, which bacteria may be genetically engineered to express a heterologous protein or to overexpress an endogenous protein, various host animals may be immunized by injection with an incapacitated whole cell immunogenic composition comprising the bacterium incapacitated by infection with a lysis-defective phage.

Such host animals may include, but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen. For the production of polyclonal antibodies, host animals such as those described above, may be immunized by injection with an incapacitated whole cell bacterial composition of the invention. The composition may be supplemented with adjuvants.

The antibody titer in the immunized subject can be monitored over time by standard techniques, such as with an enzyme linked immunosorbent assay (ELISA) using immobilized polypeptide. If desired, the antibody molecules can be isolated from the mammal (e.g., from the blood) and further purified by well-known techniques, such as protein A chromatography to obtain the IgG fraction. Antibodies specific for an antigen, or fragment thereof, particularly for a recombinant antigenic molecule expressed by genetically engineered bacteria, can be selected for (e.g., partially purified) or purified by, e.g., affinity chromatography.

For example, a recombinantly expressed and purified (or partially purified) protein antigen is produced in genetically engineered bacteria as described herein, and covalently or non-covalently coupled to a solid support such as, for example, a chromatography column. The column may then be used to affinity purify antibodies specific for the proteins from a sample containing antibodies directed against a large number of different epitopes, thereby generating a substantially purified antibody composition, i.e., one that is substantially free of contaminating antibodies. By a substantially purified antibody composition is meant, in this context, that the antibody sample contains at most only 30% (by dry weight) of contaminating antibodies directed against epitopes other than those on the desired protein or polypeptide of interest, and preferably at most 20%, yet more preferably at most 10%, and most preferably at most 5% (by dry weight) of the sample is contaminating antibodies. A purified antibody composition means that at least 99% of the antibodies in the composition are directed against the desired antigenic protein or polypeptide.

Monoclonal antibodies, which are homogeneous populations of antibodies to a particular antigen, may be obtained by any technique that provides for the production of antibodies by, for example, continuous cell lines in culture. These include, but are not limited to, the hybridoma technique of Kohler and Milstein, (1975, Nature 256, 495–497; and U.S. Pat. No. 4,376,110), the human B-cell hybridoma technique (Kosbor et al., 1983, Immunology Today 4, 72; Cole et al., 1983, Proc. Natl. Acad. Sci. USA 80: 2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the desired mAb may be cultivated in vitro or in vivo. Production of high titers of mAbs in vivo makes this the presently preferred method of production.

Uses of Antibodies Directed Against Inactivated Bacteria

The antibodies generated against the incapacitated whole cell immunogenic bacterial composition of the invention have potential uses in diagnostic immunoassays, passive immunotherapy, and generation of antiidiotypic antibodies. In one embodiment, the composition used to generate the antibodies comprises bacteria genetically engineered to express a heterologous protein or to overexpress an endogenous protein.

The generated antibodies may be isolated by standard techniques known in the art (e.g., immunoaffinity chromatography, centrifugation, precipitation, etc.) and used in diagnostic immunoassays to detect the presence of cancerous cells or viruses, bacteria, fungi or parasites of medical or veterinary importance in human or animal tissues, blood, serum, etc. The antibodies may also be used to monitor treatment and/or disease progression. Any immunoassay system known in the art, such as those listed herein, may be used for this purpose including but not limited to competitive and noncompetitive assay systems using techniques such as radioimmunoassays, ELISA (enzyme linked immunosorbent assays), "sandwich" immunoassays, precipitin reactions, gel diffusion precipitin reactions, immunodiffusion assays, agglutination assays, complement-fixation assays, immunoradiometric assays, fluorescent immunoassays, protein A immunoassays and immunoelectrophoresis assays, etc., where such immunoassays are known in the art.

The vaccine preparations of the present invention can also be used to produce antibodies for use in passive immunotherapy, in which short-term protection of a host is achieved by the administration of pre-formed antibody directed against a heterologous organism.

The antibodies generated by the vaccine preparations of the present invention can also be used in the production of antiidiotypic antibody. The antiidiotypic antibody can then in turn be used for immunization, in order to produce subpopulation of antibodies that bind the initial antigen of the pathogenic microorganism (Jerne, N. K., 1974, Ann. Immunol. (Paris) 125c:373; Jerne, N. K., et al., 1982, EMBO 1:234).

Formulations, Routes of Administration and Dosages

The vaccines of the invention can be formulated in any suitable manner. In general, the vaccines of the invention can be administered orally, nasally, nasopharyngeally, parenterally, enterically, gastrically, topically, transdermally, subcutaneously, intramuscularly, in tablet, solid, powdered, liquid, aerosol form, locally or systemically, with or without added excipients. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

It is recognized that the polypeptides and related compounds described above, when administered orally, must be protected from digestion. This can be accomplished either by mixing or packaging the incapacitated bacterium in an appropriately resistant carrier such as a liposome. The preparations may also be provided in controlled release or slow-release forms for release and administration of the antigen preparations as a mixture or in serial fashion.

The incapacitated vaccines of the invention are generally provided in compositions with a pharmaceutically acceptable excipient. Various pharmaceutically acceptable excipients are well known in the art. As used herein, "pharmaceutically acceptable excipient" includes any material which, when combined with an active ingredient of a composition, allows the ingredient to retain biological activity and without causing disruptive reactions with the subject's immune system.

Exemplary pharmaceutically carriers include sterile aqueous of non-aqueous solutions, suspensions, and emulsions. Examples include, but are not limited to, any of the standard pharmaceutical excipients such as a phosphate buffered saline solution, water, emulsions such as oil/water emulsion, and various types of wetting agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

A composition comprising a bacteriophage of the invention may also be lyophilized using means well known in the art, for subsequent reconstitution and use according to the invention.

Also of interest are formulations for liposomal delivery, and formulations comprising microencapsulated whole cell bacterial vaccine. Compositions comprising such excipients are formulated by well known conventional methods (see, for example, Remington's Pharmaceutical Sciences, Chapter 43, 14th Ed., Mack Publishing Col, Easton Pa. 18042, USA).

In general, the pharmaceutical compositions can be prepared in various forms, such as granules, tablets, pills, suppositories, capsules (e.g. adapted for oral delivery), microbeads, microspheres, liposomes, suspensions, salves, lotions and the like. Pharmaceutical grade organic or inorganic carriers and/or diluents suitable for oral and topical use can be used to make up compositions comprising the therapeutically-active compounds. Diluents known to the art include aqueous media, vegetable and animal oils and fats. Stabilizing agents, wetting and emulsifying agents, salts for varying the osmotic pressure or buffers for securing an adequate pH value.

The pharmaceutical composition can comprise other components in additional to the bacteriophage. In addition, the pharmaceutical compositions may comprise more than one bacteriophage, for example, two or more, three or more, five or more, or ten or more different bacteriophage, where the different bacteriophage may be specific for the same or different bacteria. As noted above, the bacteriophage can be administered in conjunction with other agents, such as a conventional antimicrobial agent (see table above). In some embodiments, it may be desirable to administer the bacteriophage and antibiotic within the same formulation.

The compositions are administered to an animal that is at risk from acquiring a disease caused by the bacterial pathogen to prevent or at least partially arrest the development of disease and its complications. An amount adequate to accomplish this is defined as a "therapeutically effective dose." Amounts effective for therapeutic use will depend on, e.g., the antigen composition, the manner of administration, the weight and general state of health of the patient, and the judgment of the prescribing physician. Single or multiple doses of the compositions may be administered depending on the dosage and frequency required and tolerated by the patient, and route of administration.

Amounts for the immunization of the mixture generally range from about 0.001 mg to about 1.0 mg per 70 kilogram patient, more commonly from about 0.001 mg to about 0.2 mg per 70 kilogram patient. Dosages from 0.001 up to about 10 mg per patient per day may be used, particularly when the antigen is administered to a secluded site and not into the blood stream, such as into a body cavity or into a lumen of an organ. Substantially higher dosages (e.g. 10 to 100 mg or more) are possible in oral, nasal, or topical administration. The initial administration of the mixture can be followed by booster immunization of the same of different mixture, with at least one booster, more usually two boosters, being preferred.

The invention also contemplates that the vaccine composition comprising an incapacitated bacterial vaccine may include one or more strains of bacteria.

The vaccines can be administered to any subject, generally a mammalian subject, that has or is susceptible to, infection by a bacterial pathogen. Subjects of particular interest include, but are not necessarily limited to, humans, and domesticated animals (e.g., livestock, pets, and the like) as well as animals held in captivity (e.g., in zoos or aquatic parks).

While the subject need not be immunologically naïve, the vaccines of the invention are typically administered to a subject that is immunologically naïve with respect to the particular bacterial pathogen. In a particular embodiment, the mammal is a human child about five years or younger, and preferably about two years old or younger. The vaccine of the invention can be administered as a single dose or, where desired or necessary, the initial dose can be followed by boosters at several days, several weeks, or several months or years following the initial dose. In general, administration to any mammal is preferably initiated prior to the first sign of disease symptoms, or at the first sign of possible or actual exposure to the bacterial pathogen.

EXAMPLES

The foregoing embodiments of the present invention are further described in the following Examples. However, the present invention is not limited by the Examples, and variations will be apparent to those skilled in the art without departing from the scope of the present invention. In particular, any bacteria and phage known to infect said bacteria can be substituted in the experiments of the following examples. The following examples are put forth so as to provide those of ordinary skill in the art with a complete disclosure and description of how to make and use the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Creation of Lys Minus T4 Phase

The nucleotide sequence of the lysozyme (e) gene of bacteriophage T4 together with 130 additional nucleotides on each side was reported by Owen et al (J. Mol. Biol. 165, 229, 1983). The DNAs corresponding to 100 nucleotides of the upstream and downstream regions of the e gene are isolated by PCR and cloned into the ampicillin-resistant plasmid pUC 18 with unique restriction sites (Xba I and Pst I) between the two regions ((Sambrook, J. et al Molecular Cloning: A Laboratory Manual, $2^{nd}$ ed. Cold Spring Harbor Laboratory Press, Cold Spring Harbor, N.Y.). A DNA cassette containing the gene for a mutant form of the green fluorescent protein (GFP) which fluoresces 40-fold more brightly than the wild type protein, is generated as an Xba I-Pst I fragment from plasmid pmut2 carrying gfp (Cormack, B. P., Valdivia, R. H. and Falkow, S. Gene 173, 33, 1996) and introduced between the upstream and downstream sequences of the lysozyme gene in pUC18 (pGG8). The promoter and terminator for the expression of GFP in this cassette are replaced by the early promoter of the T4 dihydrofolate reductase gene frd (Rosenberg, M. and Court, D. Ann. Rev. Genet. 13, 319, 1979) at the 5' end and the transcription terminator situated between genes 44 and 45 of T4 (Spicer and Konigsberg in Bacteriophage T4 eds. Mathews, Kutter, Mosig and Berget, American Society for Microbiology, Washington, D.C., 1983, pp. 299) at the 3' end, respectively. The frd promoter is in the immediate early class of T4 promoters that are among the first to be expressed in bacterial cells infected with T4. The host RNA polymerase is used for transcription from this promoter.

This plasmid pGG8 is transformed into *E. coli* HB101 cells by the RbCl method and selected for ampicillin resistance. *E. coli* HB101 cells harboring the plasmid pGG8 with the mutant lysozyme gene is then infected with wild-type T4 phage at a low multiplicity of infection. During replication, some of it recombines with the mutant lysozyme gene carried on the plasmids in the cells to yield Lys minus phage. It is likely that recombination in any cell will not be 100% efficient. Both types of phages are collected by lysing the bacterial cells with chloroform, and the Lys minus phage is separated from the wild-type by plaque purification. Each plaque is then tested to see if it is wild-type or Lys minus. Lys minus phages can be identified by the green fluorescence of replica plates under UV since GFP is expressed under the T4 early promoter. This can be further confirmed by testing the phage from each plaque on normal *E. coli* HB101 as well as cells expressing the lysin gene described below. Whereas wild-type phage kills both hosts, Lys minus phage kills only the host cells expressing lysin.

Example 2

Production of Lys Minus T4 Phase in *E. coli*

The two-gene lysis system of the Pneumococcal phage Cp-1 has been cloned and expressed in *E. coli* (Martinet al. J. Bacteriol. 180, 210(1998). PCR using Cp-1 DNA as the template generates DNA fragments containing the cpl1 (lysin) gene or the cassette cph1-cpl1 (holin-lysin) genes, in which the genes retain their own ribosome-binding sites. Using appropriate oligonucleotides, Sac II and Sac I restriction sites are created at the 5' and 3' ends of the PCR fragments for cloning into plasmid pNM185 (Mermod et al. J. Bacteriol. 167, 447(1986)). The cpl1 gene or the cassette containing cph1 and cpl1 genes are expressed under the control of a positively regulated promoter (Pm) of the meta pathway operon of the TOL plasmid. Transcription of the genes from Pm is specifically induced by the product of the xylS regulator gene only when effector molecules like 3-methyl benzoate are present. Transformation of *E. coli* HB101 cells with the pNM185 plasmids carrying the cpl1 or cph1-cpl1 cassette is carried out by the RbCl method ((Sambrook et al. *Molecular Cloning: A Laboratory Manual,* $2^{nd}$ ed. Cold Spring Harbor Laboratory, Cold Spring Harbor, N.Y.(1989)). The transformed *E. coli* HB101 cells are grown in LB broth or other suitable medium and inoculated with the Lys minus T4 phage. At the appropriate time, the expression of cpl1 or the cph1-cpl1 cassette on the pNM185 plasmid is induced by the addition of 2 mM 3-methyl benzoate to effect release of the Lys minus T4 phage progeny.

Example 3

Creation of Plasmid pGMB021 for Use in Lys Minus Recombinant Phase Generation Materials and Methods. Tag DNA polymerase, dNTP's, Calf Intestinal Phosphatase, Restriction enzymes, primers and T4 DNA ligase were procured from Bangalore Genei Pvt. Ltd (BGPL), Bangalore. pRSET vectors were from Invitrogen Ltd, USA.

The ligations were performed with vector: insert ratio of 1:10 M. The PCR products along with digested vectors were purified from agarose gel using Qiagen gel extraction kit reagents unless mentioned otherwise.

Construction of T4 lysozyme clone in T7 promoter based pRSETB vector (pRSETB-T4L). PCR amplification of the lysin gene of T4 was performed with the wild type T4 phage obtained from BGPL, using the following primers:

```
GMB1:  Forward 5' CG GAA TTC CAT ATG AAT ATA TTT GAA ATG TTA CGT 3'    (SEQ ID NO:1)

GMB2:  Reverse 5' AA AGC GGC CGC AAG CTT TAG ATT TTT ATA CGC GTC CCA 3'    (SEQ ID NO:2)
```

Initial denaturation was at 95° C. for 4 min, followed by 30 cycles of denaturation at 95° C. for 30 sec, annealing at 55° C. for 30 sec, and extension at 72° C. for 30 sec. The contents were finally extended for 7 min at 72° C.

Next, the PCR product obtained was purified and klenow filled in before ligation to pRSETB vector digested with PvuII and dephosphorylated with CIP. The vector to insert ratio was maintained at 1:10 M. The ligation was performed at 22° C. for 5 hours and then DH5 alpha competent cells were transformed with the above ligation mix. Transformants were then selected on LB amp plate (100 ug/ml final concentration) at 37° C. overnight. The transformants were screened by Pool colony PCR and the positive clones were then checked for restriction digestion after DNA isolation.

Figure 2:
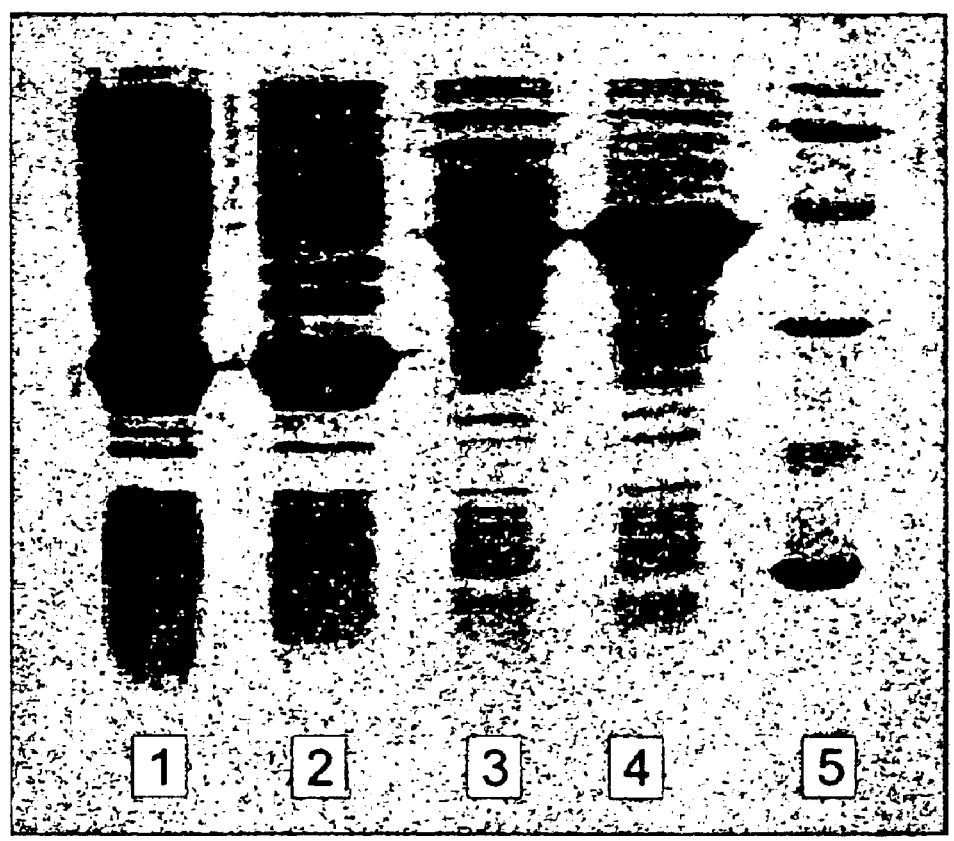
FIG. 2 illustrates SDS-PAGE of the gene products produced by plasmids pGMB011 and pGMB021 (Lane 1: pGMB011, Uninduced; Lane 2: pGMB011, Induced; Lane 3: pGMB021, Uninduced; Lane 4: pGMB021, Induced; Lane 5: 14–97 KDa marker).

The DNA of the positive clones was sequenced by ABI Prism of Pharmacia. The above clone expressed T4 lysozyme protein as seen on SDS-PAGE gel. The protein was a His tagged lysin protein of 25 KDa as expected (see FIG. 2, lanes 1 and 2). PGMB011 was selected for further use.

Construction of GFP as his tag fusion protein in pRSETA vector (pRSETA-GFP). To interrupt the lysin gene with a reporter gene, GFP gene was chosen. First, the GFP gene was amplified from pUC-GFP plasmid in the GFP teaching kit of BGPL, using the following primers:

```
GMB5:  Forward 5' CC GGA ATT CAT ATG AGT AAA GGA GAA GAA CTT TTC 3'  (SEQ ID NO:3)

GMB6:  Reverse 5' CC GGA ATT CAT TTA TTT GTA TAG TTC ATC CAT GCC 3'  (SEQ ID NO:4)
```

Initial denaturation was at 95° C. for 4 min, followed by 30 cycles of denaturation at 94 deg C. for 30 sec, annealing at 60° C. for 30 sec and extension at 72° C. for 30 sec. The final extension was at 72° C. for 7 min. The purified product was digested with EcoR1 and then ligated with pRSETA cut with EcoR1.

The clones were then screened by Pool colony PCR for GFP and small scale expression of GFP was seen on SDS-PAGE. All the clones were checked under UV light for the GFP fluorescence which indicated that the clone has GFP in the correct orientation with respect to the T7 promoter. The size of the GFP protein was 36 KDa as expected.

Interruption of the T4 lysin gene with GFP in frame with the 5' end of the T4 lysin gene to construct pGMB021. The GFP fragment from the pRSETA-GFP clone was then subcloned into partially digested pGMB011 (a pRSETB-T4L vector produced above) with EcoR1. The transformants were screened for PCR with GMB5/GMB6 and then checked by small scale expression of the his-tagged lysin-GFP fusion protein. The His-tagged lysin-GFP fusion protein expressed from the above clone (42 KDa) (see FIG. 2, lanes 3 and 4) and it showed fluorescence under UV indicating that the GFP gene was intact in this construct.

Figure 3:
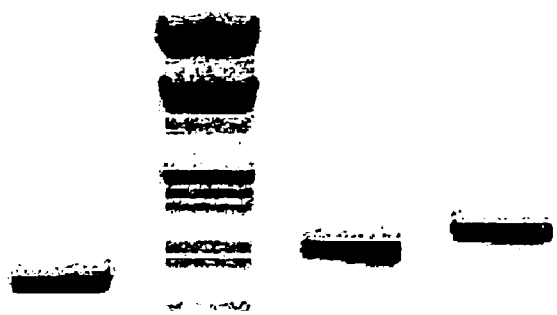
FIG. 3 illustrates PCR of the pGMB021 construct used for recombination experiments (Lane 1: GMB1/GMB2 primers.

The above clone was further tested for PCR with GMB1/GMB2 primers (T4 lysin specific primers). As expected the PCR with GMB1/GMB2 gave a product of lysine-GFP-lysin of approximately 1200 bp showing the intactness of lysin and GFP genes (FIG. 3). This clone was used in the recombination experiment described in Example 4 below.

Example 4

Generation and Isolation of Lys Minus Recombinant Phase

DH5α cells containing the plasmid pGMB021 were infected with wild T4 phage at 2.5 m.o.i. This high multiplicity of infection ensures that every cell is infected with at least one phage. After 40 minutes of incubation, chloroform (1%) was added and the lysate centrifuged. The supernatant was separated and aerated for 30 minutes at room temperature for evaporation of the residual chloroform.

The lysate was treated with DNase (50 ug/ml) for 30 min at 37° C. to digest the chromosomal and plasmid DNA, and then was titred. Next, normal E. coli cells (bearing no plasmid) were infected with the lysate at 0.1 m.o.i. This low multiplicity of infection ensures that all the infected cells contain a single phage, which in turn serves to separate the recombinant and the wild phages.

The above infection mix was incubated at 37° C. for 30 min and then centrifuged. The cell pellet and supernatant were separated. The cells containing the recombinant Lys minus phage will not lyse and were therefore be present in the cell pellet among uninfected cells. The supernatant was discarded, as this fraction was likely to contain most of the wild phages. The pellet was then resuspended in culture medium (Luria Broth) and lysed with egg-white lysozyme (10 ug/ml) and chloroform (2%). This lysate was used to infect BL21 (DE3) pLys E cells at 0.1 m.o.i. and plated on a lawn of the same cells. These cells were specifically chosen for this step since they constitutively express, from a plasmid, T7 phage lysozyme and would aid Lys minus phages to form plaques.

Two types of plaques were seen on the plate—several wild type plaques and a few minute or pin-point plaques. The pin-point plaques were picked up and resuspended in culture medium. Next, these were allowed to infect BL21

(DE3) pLysE cells and then plated on a 1:1 mixture of BL21 (DE3) pLysE (which make T7 lysozyme) and LE392 cells (no lysozyme).

Turbid areas representing the recombinant phage were distinguishable among wild type plaques on the lawn of the mixture of cells. These turbid areas were picked up. Part were resuspended in water for PCR and the remaining were resuspended in culture medium. GFP gene product was amplifiable from many of the turbid plaques (FIG. 4).

The full length T4 lysin-GFP-lysin was also amplified. However, the wild type lysin gene product was also present, indicating presence of wild phage (FIGS. 5 and 6). Selective elimination of wild phage form these lysates were done by infecting cells at low m.o.i and lysis of the cells at 40 min. At this time, the wild phage would have entered another round of infection and will be in the eclipse stage (in DNA form). Lysis of cells thus destroys the wild phage before assembly into particles. After 3–5 rounds of such elimination, the lysates were plaque-less (FIG. 7). Confirmation of the presence of the recombinant phage in such lysates and quantitation was done by estimating the number of viable cells after infection. Loss of viability of infected cells was evident upon plating the infection mix (FIG. 8).

In order to enrich the recombinant phage and avoid the use of chloroform and external supplementation of lysozyme, a temperature sensitive mutant E. coli cell type (RE 7) (which grows at 30° C. and lyses at 42° C.) was used. Enrichment of the recombinant phage to a level of ~$2 \times 10^8$/ml was attained. This preparation was used to infect a pathogenic E. coli strain at 2 m.o.i. These cells in their native state cause death of 80% of animals when injected at a dose of $10^8$ cells/mouse within 48 hours. The recombinant phage-inactivated pathogenic cells have been injected into mice to evaluate the efficacy as a whole-cell inactivated vaccine.

Example 5

Preliminary Study of the Efficacy of Lys-Minus Phase in Protection of Mice Against Experimental E. coli Infection Six to eight week old male and female Swiss Albino mice were injected intraperitoneally with a pathogenic E. coli strain that causes 100% mortality at 108 cfu. All mice died within 48 hours.

When mice were injected with $5 \times 10^7$ cells, 70–80% mortality was observed. There was no mortality, however, at $10^6$ cfu.

Mice were therefore injected with (i) $10^6$ wild type cells or (ii) $10^6$ cells that were made non-viable by infection with the Lys minus phage. After allowing ten days for the development of an immune response, the animals were challenged with wild type cells ($5 \times 10^7$ cfu) along with animals that were only administered saline and observed up to a period of 10 days. There was significant mortality in the group injected with E. coli inactivated with Lys minus phage probably due to endotoxin.

In the vehicle control group, there was 80% mortality as expected. In the group where wild type cells were used as vaccine, 20% mortality was observed indicating 80% protection. In the group where the cells had been rendered non-viable by the Lys-minus phage, there was no mortality at all indicating total protection.

| Group | No. of mice/ group | No of survivors | No of animals challenged | No of survivors | % Protection |
|---|---|---|---|---|---|
| Vehicle control (saline) | 10 | 10 | 10 | 2 | 20% |
| Wild type ($10^6$ cfu) | 10 | 10 | 10 | 8 | 80% |
| Lys-P-infected cells | 16 | 8* | 8 | 8 | 100% |

Note:
Lys-P stands for the phage that infects E. coli cells and renders it non-viable but does not lyse the cell.
*The deaths seen may be an effect of endotoxin that may have come from the compromised bacterial cells within the body. This can be avoided by using a lower number of incapacitated cells for immunization and repeating with a booster dose two weeks after the primary immunization. Further washing of the incapacitated bacterial cells prior to administration may also eliminate the problem.

Antibody Response

To check for presence of antibodies in the mice that survived in the different groups, these mice were sacrificed 7 days after the challenge dose was administered and serum was collected. Serum was collected from unchallenged vehicle control group animals served as a negative control. The serum samples were checked for reactivity to E. coli 443 cells. The presence anti-E. coli antibodies in the sera was confirmed in a standard ELISA format using a preparation of E. coli cells (Strain#MTCC443) coated onto microplate wells for capture and anti-mouse IgG conjugated to Alkaline phosphatase enzyme as reporter. Mice were scored as 'positive' for anti-E. coli antibodies against the mean of OD values of 6 negative control sera used.

All mice surviving the challenge showed presence of anti-E. Coli 443 antibodies. The Lys minus phage group was comparable to the group administered live cells. All values shown in the table below represent the mean of duplicate assays. The mean OD of control animals (6) not exposed to E. coli (uninfected control) was 0.3.

| ELISA results: | | O.D values (405 mn) | | | | | | | | |
|---|---|---|---|---|---|---|---|---|---|---|
| Sl No | Challenged Group | Mouse 1 | 2 | 3 | 4 | 5 | 6 | 7 | 8 | 9 10 |
| 1. | Live cells group | 1.19 | 1.0 | 0.87 | 1.0 | Not assayed | | | | 8 survivors |
| 2. | Lysis minus Phage | 0.6 | 0.72 | 0.83 | 0.7 | 0.9 | 0.9 | 0.6 | 0.7 | 8 survivors |
| 3. | Vehicle control | 1.2 | 0.5 | | | 2 survivors | | | | |

That which is claimed is:

1. A method of eliciting an immune response to a bacteria pathogen, the method comprising:

administering a composition to a subject susceptible to infection by a disease caused by a pathogenic bacterium, wherein the composition comprises a whole cell pathogenic bacterium, which bacterium is in a state of irreversible bacteriostasis due to infection with a Lys minus bacteriophage, said administering being in an amount effective to elicit an immune response to the pathogenic bacterium in the host.

2. The method of claim 1, wherein the pathogenic bacterium is of a genus selected from the group consisting of *Mycobacteria, Staphylococci, Vibrio, Enterobacter, Enterococcus, Escherichia, Haemophilus, Neisseria, Pseudomonas, Shigella, Serratia, Salmonella, Streptococcus, Klebsiella* and *Yersinia*.

3. A method of vaccinating a subject against disease caused by a bacterial pathogen, the method comprising:

administering to a subject susceptible disease caused by a pathogenic bacterium a composition comprising a whole cell pathogenic bacterium, which bacterium is in a state of irreversible bacteriostasis due to infection with a Lys minus bacteriophage, said administering being in an amount effective to elicit an immune response to the pathogenic bacterium in the subject.

4. The method of claim 3, wherein the pathogenic bacterium incapacitated by infection with a Lys minus bacteriophage is genetically engineered to overexpress an endogenous antigen.

5. The method of claim 3, wherein the pathogenic bacterium is of a genus selected from the group consisting of *Mycobacteria, Staphylococci, Vibrio, Enterobacter, Enterococcus, Escherichia, Haemophilus, Neisseria, Pseudomonas, Shigella, Serratia, Salmonella, Streptococcus, Klebsiella* and *Yersinia*.

6. A composition consisting essentially of a bacterium and a pharmaceutically acceptable excipient, wherein the bacterium is in a state of irreversible bacteriostasis due to infection with a Lys minus bacteriophage.

7. The composition of claim 6, wherein the bacterium is of a genus selected from the group consisting of *Mycobacteria, Staphylococci, Vibrio, Enterobacter,*

*Enterococcus, Escherichia, Haemophilus, Neisseria, Pseudomonas, Shigella, Serratia, Salmonella, Streptococcus, Klebsiella* and *Yersinia*.

8. The method of claim 1, wherein the bacteriophage has a mutation or a deletion in a lysin gene which renders the bacteriophage incapable of producing a functional lysin protein.

9. The method of claim 3, wherein the bacteriophage has a mutation or a deletion in a lysin gene which renders the bacteriophage incapable of producing a functional lysin protein.

10. The composition of claim 6, wherein the Lys minus bacteriophage does not produce a functional lysin protein due to the presence of a mutation in the lysin gene.

11. The composition of claim 6, wherein the Lys minus bacteriophage does not produce a functional lysin protein due to deletion of all or a portion of the lysin gene.

12. The composition of claim 6, wherein the composition is sterile.

13. A composition comprising a bacterium and a pharmaceutically acceptable excipient, wherein the bacterium is in a state of irreversible bacteriostasis due to infection with a Lys minus bacteriophage.

14. The composition of claim 13, wherein the bacterium is of a genus selected from the group consisting of *Mycobacteria, Staphylococci, Vibrio, Enterobacter, Enterococcus, Escherichia, Haemophilus, Neisseria, Pseudomonas, Shigella, Serratia, Salmonella, Streptococcus, Klebsiella* and *Yersinia*.

15. The composition of claim 13, wherein the Lys minus bacteriophage does not produce a functional lysin protein due to the presence of a mutation in the lysin gene.

16. The composition of claim 13, wherein the Lys minus bacteriophage does not produce a functional lysin protein due to deletion of all or a portion of the lysin gene.

17. The composition of claim 13, wherein the composition is sterile.

* * * * *

SEQUENCE LISTING

<160> NUMBER OF SEQ ID NOS: 4

<210> SEQ ID NO 1
<211> LENGTH: 35
<212> TYPE: DNA
<213> ORGANISM: Artificial Sequence
<220> FEATURE:
<223> OTHER INFORMATION: primer

<400> SEQUENCE: 1
cggaattcca tatgaatata tttgaaatgt tacgt               35

<210> SEQ ID NO 2
<211> LENGTH: 38
<212> TYPE: DNA
<213> ORGANISM: Artificial Sequence
<220> FEATURE:
<223> OTHER INFORMATION: primer

<400> SEQUENCE: 2
aaagcggccg caagctttag atttttatac gcgtccca            38

<210> SEQ ID NO 3
<211> LENGTH: 35
<212> TYPE: DNA
<213> ORGANISM: Artificial Sequence
<220> FEATURE:
<223> OTHER INFORMATION: primer

<400> SEQUENCE: 3
ccggaattca tatgagtaaa ggagaagaac ttttc                35

<210> SEQ ID NO 4
<211> LENGTH: 35
<212> TYPE: DNA
<213> ORGANISM: Artificial Sequence
<220> FEATURE:
<223> OTHER INFORMATION: primer

<400> SEQUENCE: 4
ccggaattca tttatttgta tagttcatcc atgcc                35